(12) United States Patent
Agio et al.

(10) Patent No.: US 10,571,398 B2
(45) Date of Patent: Feb. 25, 2020

(54) DEVICE FOR THE BEAMING OF LIGHT EMITTED BY LIGHT SOURCES, IN PARTICULAR FLUORESCENCE OF MOLECULES

(71) Applicant: CONSIGLIO NAZIONALE DELLE RICERCHE, Rome (IT)

(72) Inventors: Mario Agio, Rome (IT); Costanza Toninelli, Rome (IT); Simona Checcucci, Rome (IT); Fabrizio Sgrignuoli, Rome (IT); Sahrish Rizvi, Rome (IT); Pietro Ernesto Lombardi, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 95 days.

(21) Appl. No.: 15/566,543

(22) PCT Filed: Apr. 13, 2016

(86) PCT No.: PCT/EP2016/058069
§ 371 (c)(1),
(2) Date: Oct. 13, 2017

(87) PCT Pub. No.: WO2016/166130
PCT Pub. Date: Oct. 20, 2016

(65) Prior Publication Data
US 2018/0128742 A1 May 10, 2018

(30) Foreign Application Priority Data

Apr. 14, 2015 (IT) .............................. RM2015A0155

(51) Int. Cl.
*G01N 21/64* (2006.01)
*B82Y 20/00* (2011.01)

(52) U.S. Cl.
CPC ............ *G01N 21/645* (2013.01); *B82Y 20/00* (2013.01); *G01N 2021/6463* (2013.01); *G01N 2021/6465* (2013.01); *G01N 2021/6484* (2013.01)

(58) Field of Classification Search
CPC ......... G01N 21/645; G01N 2021/6463; B82Y 20/00
See application file for complete search history.

(56) References Cited

U.S. PATENT DOCUMENTS

2012/0091365 A1   4/2012  Moerner et al.
2013/0286633 A1 * 10/2013  Rodriguez .............. H01L 33/50
                                                          362/84

FOREIGN PATENT DOCUMENTS

EP          2 477 240 A1     7/2012
WO      WO 2015/019220 A1    2/2015

OTHER PUBLICATIONS

Terukazu Kosako, et al., "Directional emission of light from a nano-optical Yagi-Uda antenna", arxiv.org, Cornell University Library, 201, Olin Library Cornell University, Ithaca, NY 14853, Oct. 13, 2009, 4 pages.

(Continued)

*Primary Examiner* — Thanh Luu
(74) *Attorney, Agent, or Firm* — Muncy, Geissler, Olds & Lowe, P.C.

(57) ABSTRACT

The present invention concerns a device constituted by a planar optical antenna which allows to beam and collect light emitted from various light sources, including light-emitting devices (LEDs), fluorescent markers and single-photon sources. By considering the light source as a light receiver and using reciprocity, the device can also be used to (Continued)

improve the absorption of light by various receivers, including molecules. This device is in particular suitable for in-vitro diagnostics (IVD).

18 Claims, 28 Drawing Sheets

(56) References Cited

OTHER PUBLICATIONS

Ivan S. Maksymov, et al., "Optical Yagi-Uda nanoantennas", Nanophotonics, vol. 1, No. 1, Jan. 1, 2012, pp. 65-81.

* cited by examiner

DEVICE FOR THE BEAMING OF LIGHT EMITTED BY LIGHT SOURCES, IN PARTICULAR FLUORESCENCE OF MOLECULES

BACKGROUND OF THE INVENTION

Field of the Invention

The present invention concerns a device for the beaming of light emitted by light sources, in particular fluorescence of molecules.

More in detail, the present invention concerns a device constituted by a planar optical antenna which allows beaming and collecting light emitted from various light sources, including light-emitting devices (LEDs), fluorescent markers and single-photon sources. By considering the light source as a light receiver and using reciprocity, the device can also be used to improve the absorption of light by various receivers, including molecules. This device is in particular suitable for in-vitro diagnostics.

Brief Discussion of the Related Art

The past decades have witnessed a tremendous attempt in exploring collection strategies for light-emitting devices (LED) and single-photon sources, such as single molecules, for example: optical resonators and solid-immersion lenses (W. L. Barnes et al., Eur. Phys. J. D 18, 197 (2002)), grating structures (S. C. Kitson et al., Opt. Commun. 122, 147 (1996), H. Rigneault et al., Opt. Lett. 24, 148 (1999)) and photonic crystals (M. Rattier et al., Opt. Quantum Electron. 34, 79 (2002), M. Zelsmann et al., Appl. Phys. Lett. 83, 2542 (2003)). More recently, similar attempts have emerged in biophotonics, where several methods have been proposed to improve single-molecule fluorescence detection while reducing the probed volume.

Nanophotonics-based detection offers several advantages in comparison to optical microscopy: i) sub-diffraction limited sensing volumes, ii) sensitivity, iii) speed and flexibility, iv) integrability, scalability and cost effectiveness. FIG. 1 illustrates some of the most advanced nanophotonics concepts that are currently being explored for these purposes.

Despite the enormous progress, designing, manufacturing and testing, nanophotonics concepts that interface tiny sensing volumes to low NA (Numerical Aperture) collection optics (e.g. optical fibers), still require a substantial research effort. Moreover, despite the commercial availability of surface-plasmon-polariton-based sensing and a number of proofs of concept (A. M. Armani et al., Science 317, 783 (2007)), many advanced nano-photonics concepts have not yet substantially contributed to the advancement of in-vitro diagnostics (IVD) and solid-state lighting, to cite a few.

From the photonic point of view, light detection from a sub-wavelength emitter may be seen as an antenna problem, where the light radiated by a Hertzian dipole has to be efficiently collected by a receiver. According to the Frijs formula (C. A. Balanis, Antenna Theory—Analysis and Design (Wiley, 2005) pages 94-96), the power T transferred to the detector is:

$$T \propto \eta_t D_t D_r \frac{\lambda^2}{4\pi d^2} \quad (1)$$

wherein $\eta_t$ is the radiation efficiency of the transmitting antenna, $D_t$ and $D_r$ respectively are the directivity of the transmitting and receiving antennas. The last term represents the attenuation for an isotropic radiator as a function of wavelength $\lambda$ and distance d between the two antennas. If the receiving antenna, i.e. the collection optics, is located in the far-field region where $d \gg \lambda$, the power transfer is not negligible if at least one of the directivities is much larger than one. A dye molecule in a homogenous medium yields $D_t = 1.5$, hence the need for high-NA collection optics. Therefore, a goal would be to design the electromagnetic environment around the emitter in such a way that $D_t \gg 1$ and $D_r$ may be accordingly reduced.

This could be used in biochips for IVD. Traditionally, the approach in the field is to provide fluidic and optical designs that are physically separated in a sensor. Therefore, another goal would be the integration of fluidic and optical functionality in a single biochip.

There have been several interesting proposals to improve the collection efficiency of nanoscale light emitters, although only recently the attention has moved to concepts inherited from antenna theory. In what follows we describe only the most relevant results that have been published in the past few years. The papers of K. G. Lee et al. Nat Photonics 5, 166 (2011) and Xue-Wen Chen et al., Opt. Lett. 36, 3545 (2011) shows how to achieve theoretically 99% collection efficiency with a layered structure, with experiments showing 96% at best. However, the radiation pattern is not beamed such that still a high NA objective is required in order to obtain large collection efficiencies. Furthermore, they work on the leaky modes of the layered geometry in order to ensure that all the emitter power is radiated.

F. Bigourdan et al., Opt. Express 22, 2337 (2014) is another work where a planar geometry is used to improve the collection efficiency. The top layer is a finite geometry, which implies the emitter needs to be placed very accurately in the plane of the device. Moreover, the radiation pattern is not single-lobed: it has 2 lobes which make the collection with low-NA optics challenging.

On the side of commercial devices, the example of Ligthcycler® of Roche Diagnostics boasts a footprint of more than 300 customers in the market today. The instrument performs a PCR amplification of the sample with a multiwell plate and reads the result using fluorescence. PCR is required because the optical readout scheme is not sensitive enough. The amplification process is performed on the whole sample, which does not allow the usage of different microbial detection schemes. Furthermore, as shown in FIG. 2 of the paper, the fluorescence excitation and collection setup relies essentially on geometrical optics, meaning that the sensitivity is fundamentally limited by the extremely low collection efficiency. Moreover, there is no automated disposal of sample and reagents, the overcome of amplification steps, which are time consuming and eventually lead to an error prone method, the possibility to perform and read on the same instrument and at the same time different microbial tests. FIG. 2 is a schematic overview of the LightCycler® 480 Instrument's detection unit.

SUMMARY OF THE INVENTION

It is object of the present invention to provide a device by which the emission of light from sources such as LEDs, fluorescent markers and single-photon sources, e.g. single molecules, solves the above mentioned problems of the prior art.

It is subject-matter of the present invention a device according to the enclosed claims.

BRIEF DESCRIPTION OF THE DRAWINGS

The invention will be now described by way of illustration but not by way of limitation, with particular reference to the drawings of the enclosed figures, wherein.

Figure 1:
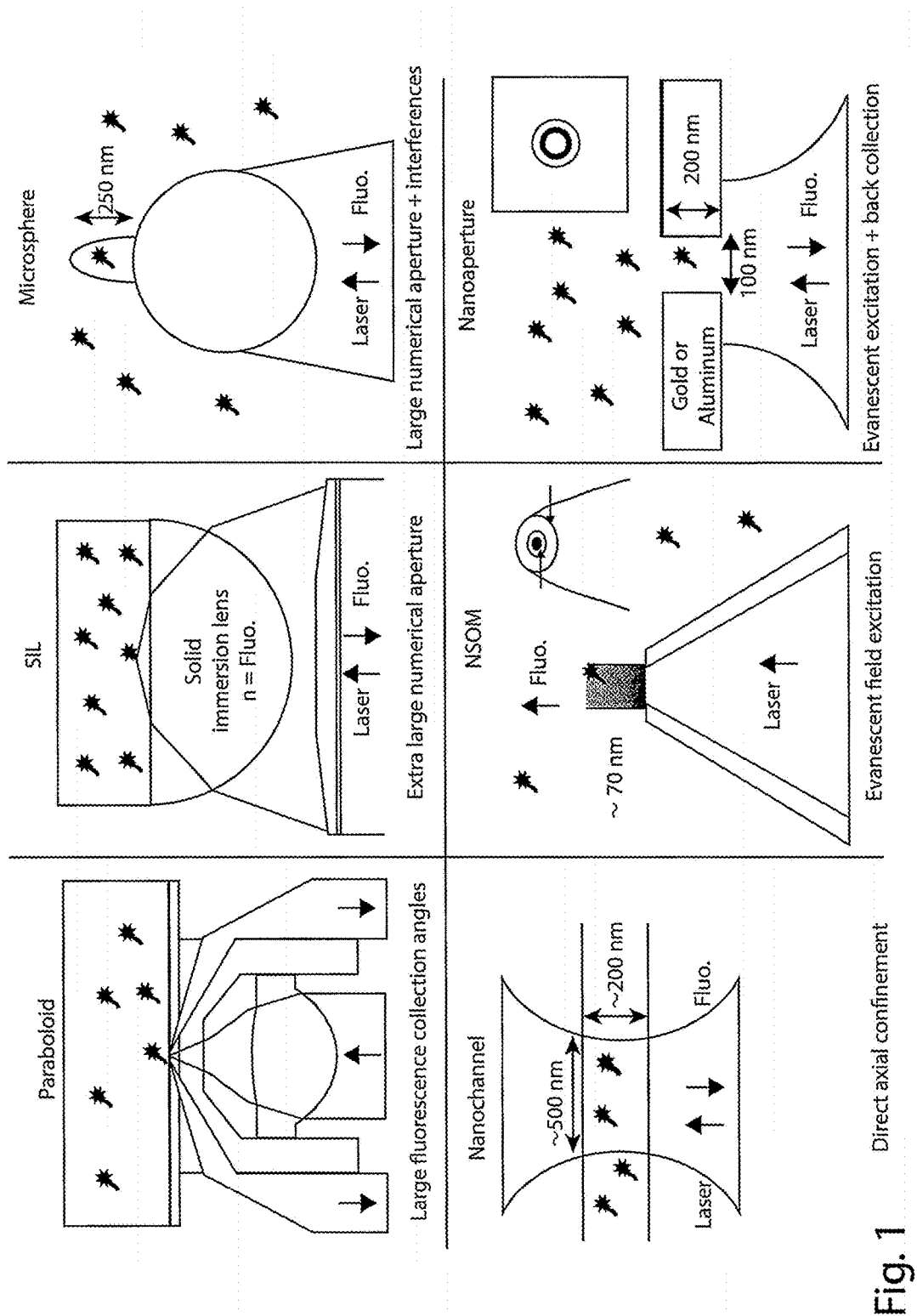
FIG. 1 shows photonics designs used for improving single-molecule fluorescence detection (source: J. Wenger and H. Rigneault, Intl. J. Mol. Sci. 11, 206 (2010))

(e) Normalised power ($P_{coll}/P_{hom}$) as a function of the collection angle for the configurations of FIG. 1. The case of a Hertzian dipole with random orientation (RD) is shown by the dashed-dotted curve. $P_{hom}$ is the total power emitted by a Hertzian dipole in a homogeneous medium of refractive index n=1.5.

Figure 21:
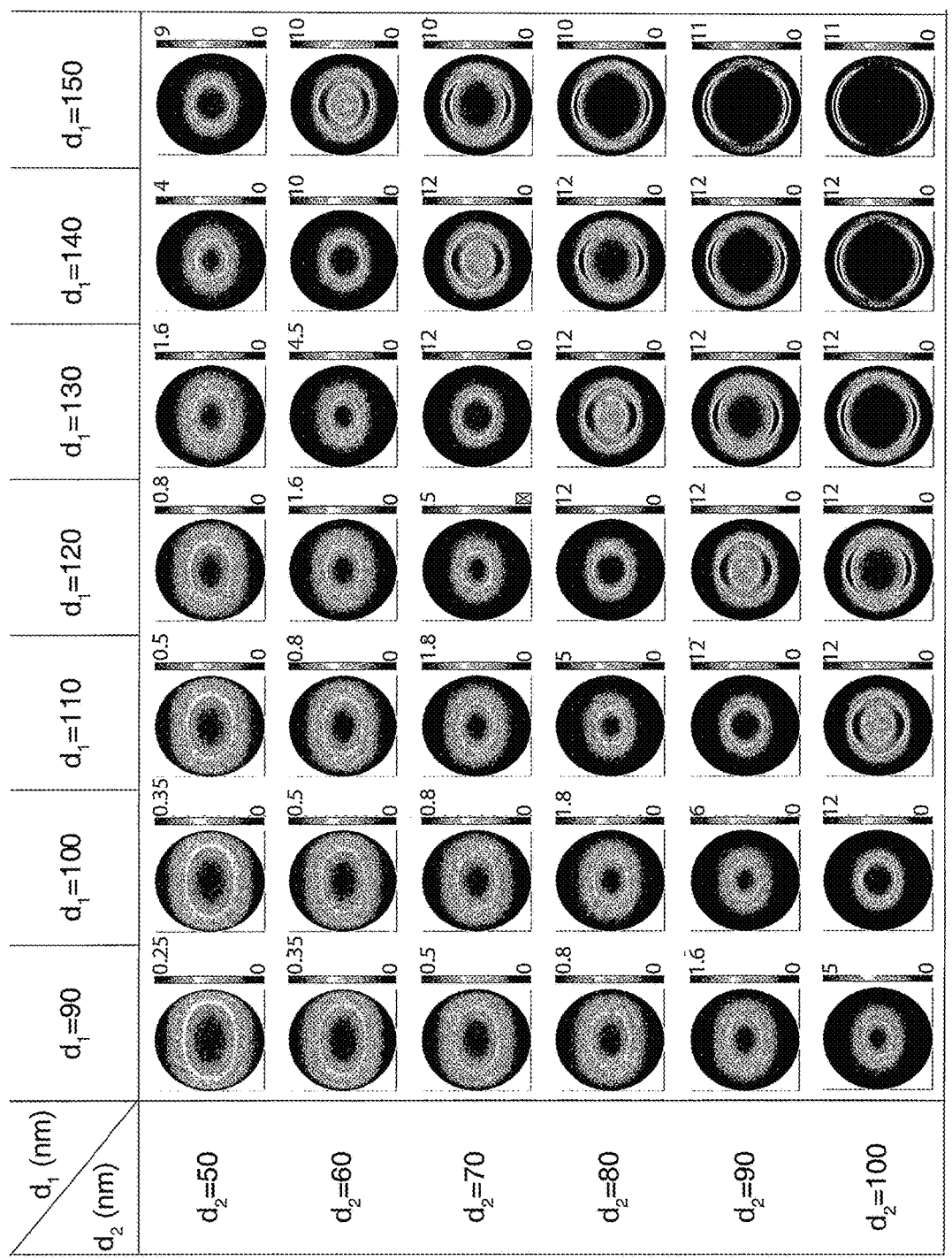
Figure 22:
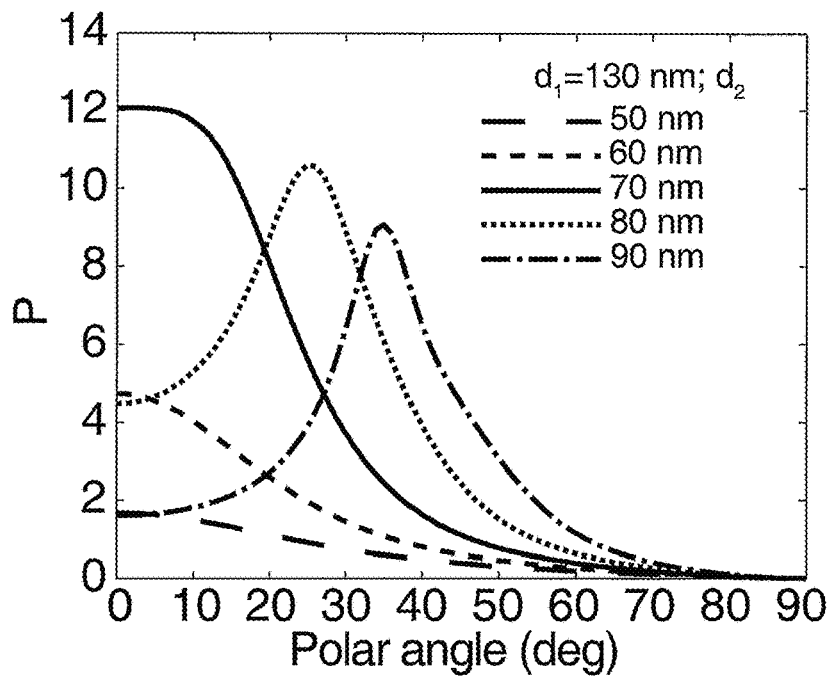

FIG. 21 shows an emission pattern as a function of the dipole position and total antenna length. Angular emission pattern of a Hertzian dipole aligned horizontally with respect to the plane of a multilayer, consisting from bottom to top of a 100-nm gold reflector, followed by a spacer layer with n=1.5 containing the dipole, and by a 20-nm gold director (top view). The antenna is surrounded by air, while $d_1$ and $d_2$ represent the distances of the dipole from the reflector and director respectively. The plots are normalized to the maximum emission of a Hertzian dipole in a homogeneous medium with n=1.5;

FIG. 22 shows performances against total antenna length. Radiated power (P) integrated over the azimuthal coordinate as a function of the polar angle for different values of the antenna length around the optimal configuration. In particular the dipole position is kept constant at $d_1$=130 nm from the reflector surface, whereas the distance to the upper director is scanned from 50 to 90 nm. The curves are normalized to the maximum value of the same quantity for the emission of a Hertzian dipole in a homogeneous medium with n=1.5.

Figure 23:
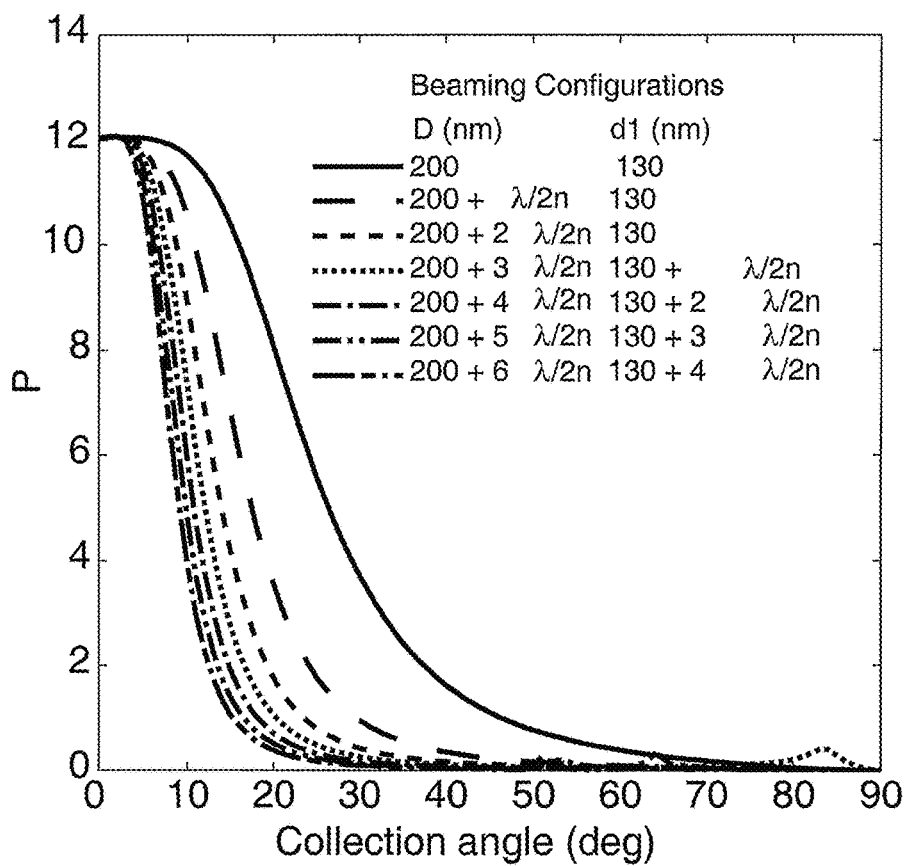

FIG. 23 shows optimal configurations with different values of the antenna length. Radiated power (P) integrated over the azimuthal coordinate as a function of the polar angle for different configurations yielding beaming. By simply scaling the shortest antenna with $\lambda/2n$ we restore the angular confinement of the radiation profile. The optimal dipole distance to the reflector ($d_1$) is accordingly modified. The curves are normalized to the maximum value of the same quantity for the emission of a Hertzian dipole in a homogeneous medium with n=1.5.

Figure 20:
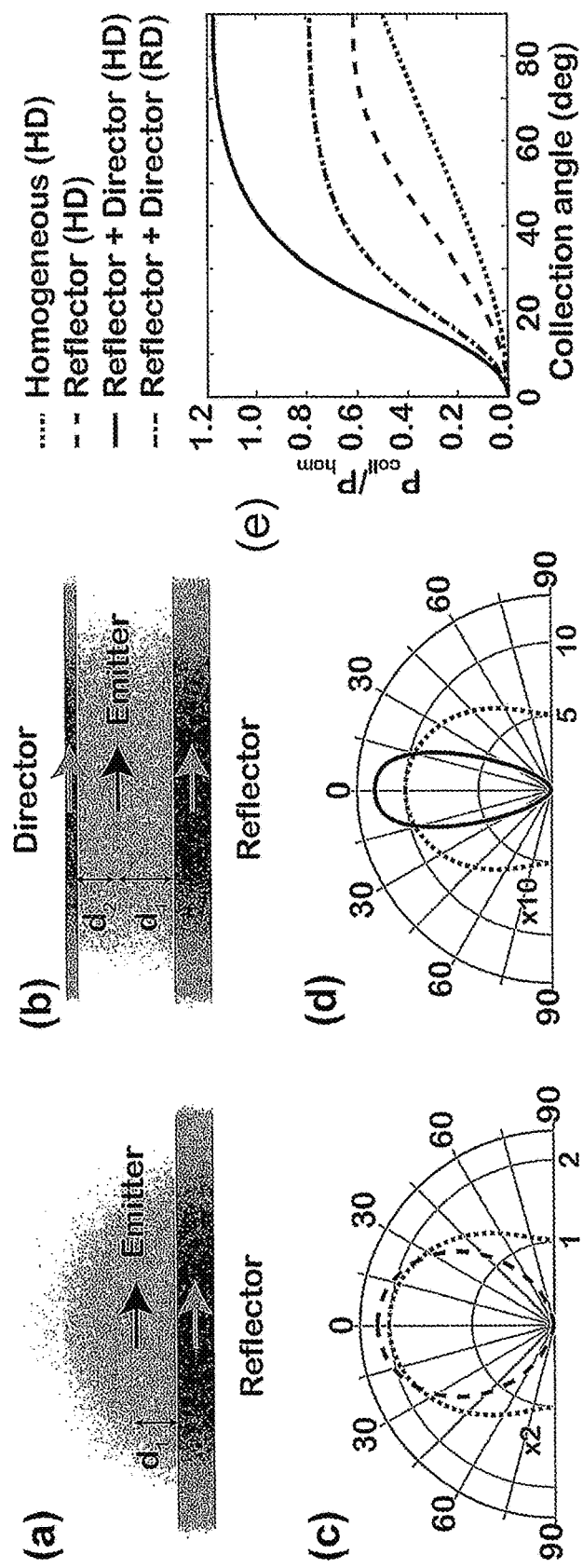
FIG. 20 shows the concept of a planar directional antenna and theoretical analysis. (a-b) Sketch of a planar directional antenna: the induced image-dipoles are identified by the gray arrows in the reflector and in the director respectively, while the source dipole is represented by a black arrow. The emitter is placed at distance $d_1$ and $d_2$ from the reflector and the director, respectively. In our study the reflector and the director are gold films of thickness 100 nm and 20 nm, respectively. The medium above the reflector has a refractive index n=1.5, while a semi-infinite air-top-layer is considered (n=1). (c-d) Radiation pattern integrated over the azimuthal coordinate as a function of the polar angle $\theta$ of a horizontal Hertzian dipole (HD), emitting at $\lambda=785$ nm, coupled to the planar directional antenna of FIG. 1, in a ($d_1=80$ nm) and b ($d_1=130$ nm and $d_2=70$ nm), respectively. The two curves are normalized by the maximum value of the same quantity for the case of a dipole in a homogeneous medium with refractive index n=1.5, which is also shown by the dotted curves.
Figure 24:
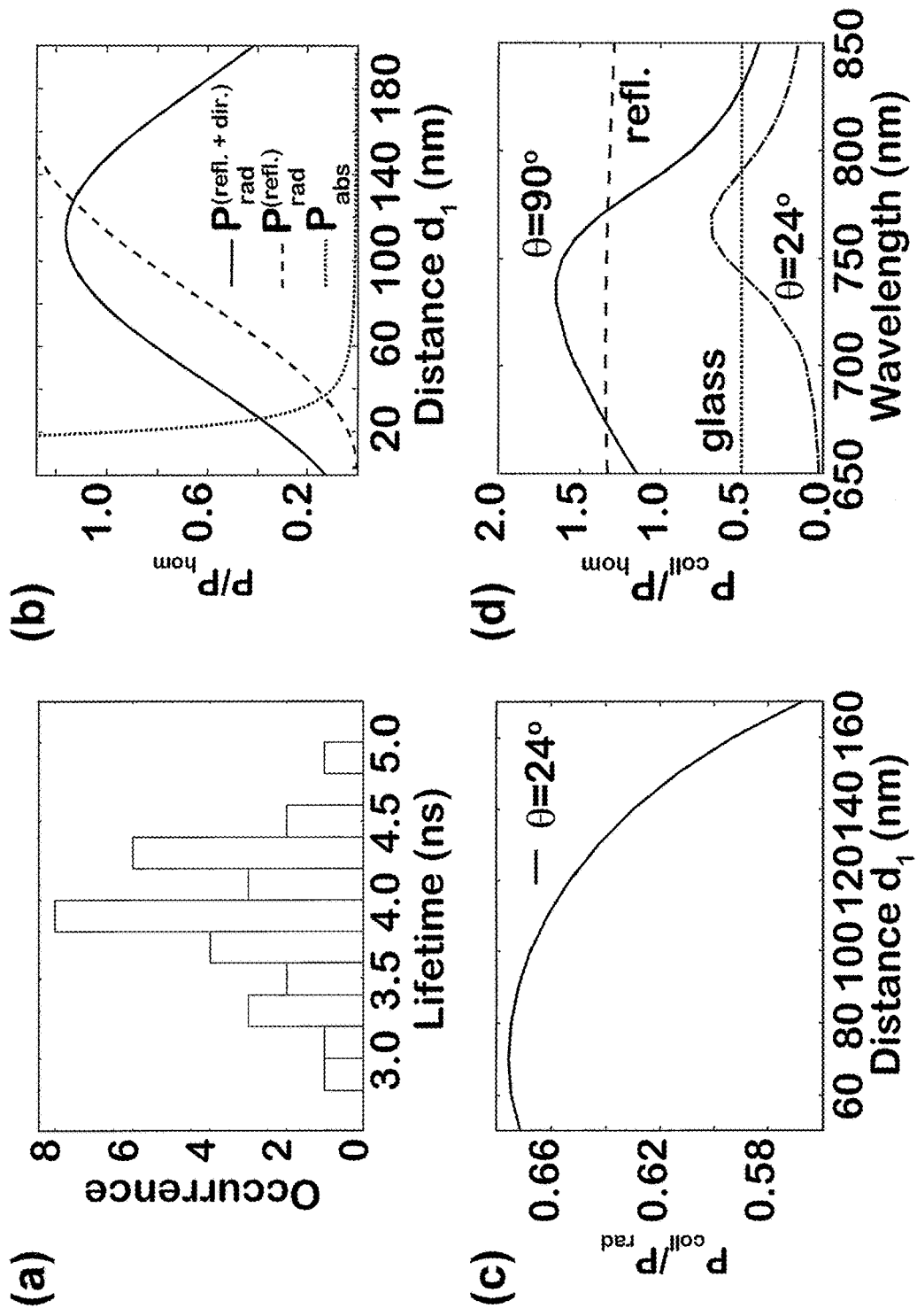

FIG. 24 shows further analysis about the antenna robustness (a) Statistical distribution of the excited-state lifetime of a DBT molecule in a Ac crystalline film when coupled to our planar optical antenna with director and reflector, as sketched in FIG. 20, in (b). (b) Normalised power radiated by a Hertzian dipole ($P_{rad}/P_{hom}$) at $\lambda$=785 nm in a medium with refractive index n=1.5 at a distance $d_1$ from a reflector (solid curve). The distance between the 100 nm-thick gold reflector and a 20 nm-thick gold director is kept constant at 200 nm. The dotted curve refers to power absorption ($P_{abs}/P_{hom}$) by energy transfer to the reflector, while the dashed curve to $P_{rad}/P_{hom}$ for the case where the Hertzian dipole is in front of a perfect mirror. The media below reflector and above director are air and glass, respectively. (c) $P_{coll}/P_{rad}$ collected up to an angle of 24° as a function of the distance $d_1$ from the reflector. The antenna parameters are the same of FIG. 20, in (c), except that the external media are interchanged. (d) $P_{coll}/P_{hom}$ collected up to θ=24° (dotted-dashed curve) and θ=90° (solid curve) as a function of wavelength for $d_1$=130 nm and the antenna parameters of FIG. 20, in (d). $P_{coll}/P_{hom}$ up to θ=90° for a Hertzian dipole in glass (dotted curve) or 130 nm from a reflector (dashed curve) is also shown.

DETAILED DESCRIPTION OF THE PREFERRED EMBODIMENTS

Introduction

One of the most exciting advances in nano-optics has been the concept, design and application of optical antennas, or nano-antennas, which represent the most sophisticated tool to enhance and direct light emission from a nanoscale source. The amount of research activity on optical antennas has grown very rapidly in the last few years, and currently spans a broad range of areas, including optics, physics, chemistry, electrical engineering, biology, and medicine, to cite a few (M. Agio and A. Alù, Optical Antennas (Cambridge University Press (2013)). Moreover, recent years have witnessed a tremendous progress in nanofabrication, which has enabled the production of complex nano-photonics structures with unprecedented design flexibility and throughput.

In the research to achieve the above object of the invention, the goal of the Inventors has been the design, manufacture and experimental investigation of optical antennas that are able to channel molecular fluorescence into a narrow radiation cone. This was thought in order to allow efficient collection by a fiber probe placed in the far field, hence opening the pathway to single-molecule detection with low-NA optics. Optical antennas offer great flexibility in engineering the radiation pattern. Therefore, another major contribution aimed at by the Inventors has been the integration of fluidic and optical functionality in a single biochip. An opto-fluidic chip may offer several advantages in comparison to conventional approaches where the fluidic and optical design are physically separated in the sensor: i) optics and fluidics are integrated in a single and disposable sensing unit, ii) design and nanofabrication may be more aggressively optimized for high-throughput and low-cost production.

Background Idea

Figure 3:
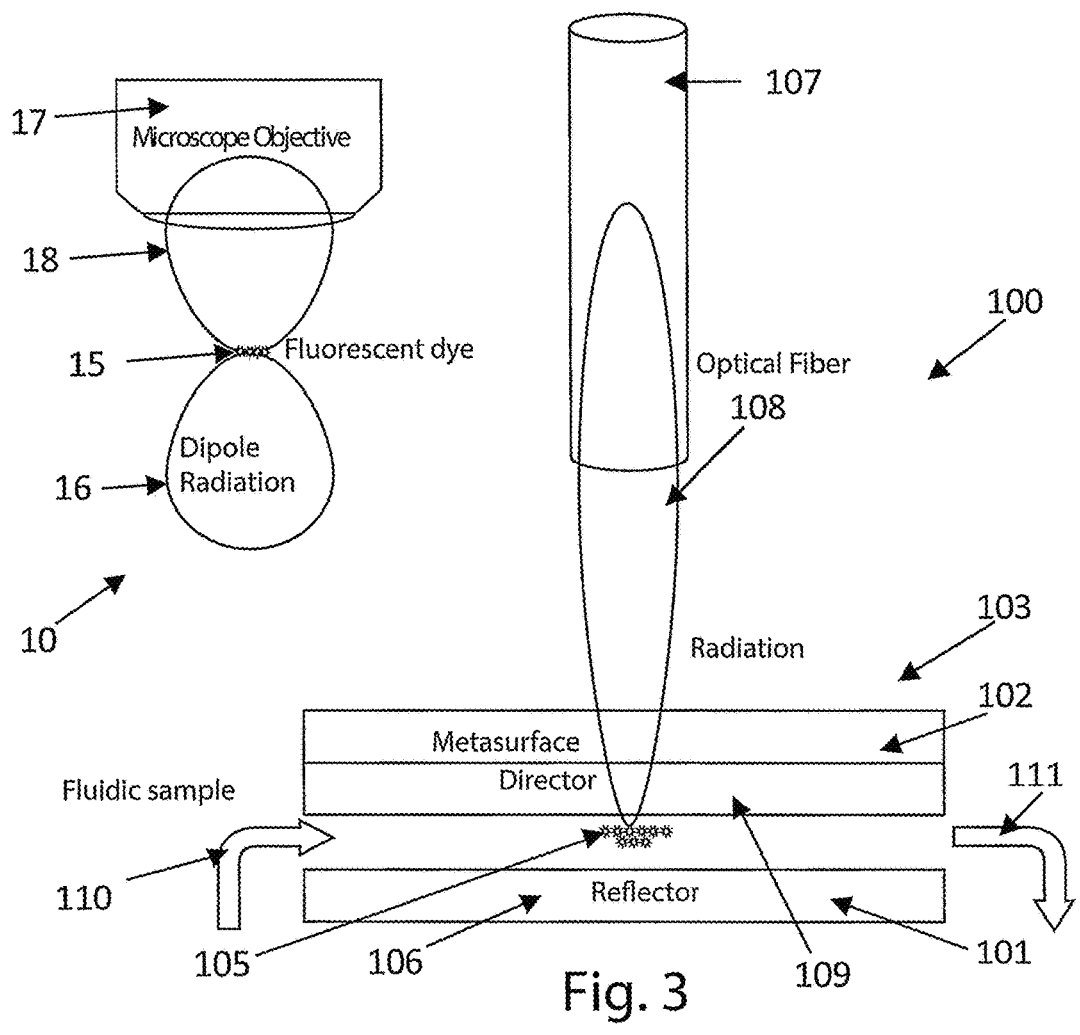
FIG. 3 shows the collection strategy of an embodiment of the invention based on the concept of a planar optical antenna (original design—2012), compared to the prior art structure of single-molecule fluorescence microscopy (inset, left); the invention antenna architecture is made of a reflector, a director and a metasurface, wherein the narrow radiation cone is efficiently collected by an optical fiber.

FIG. 3 sketches how the invention basically achieves efficient collection of molecular fluorescence based on the optical antenna concept. The inset on the left shows the typical situation of a fluorescence microscope 10, wherein a high-NA objective 17 is required in order to detect single molecules 15 that emit with a dipolar radiation pattern 16, 18.

The design strategy of the invention device 100 has been split into two main components. One part is made of a reflector 101 and a director 102 placed at a distance from both the reflector 101 and the light emitter 105 (which is, in general, a light source of any type). The latter is placed in a spacer medium 109 to space these elements apart (it is an optical passive element that does not change the wavelength of the light coming from the sources). The reflector (and possibly the director) channel fluorescence in the upper half plane. The concepts behind the invention are: 1) the positioning of the light source at an appropriate distance from a reflector in order to achieve beam forming, 2) the addition of a semi-opaque film that acts as a director in order to further enhance the directionality of the radiation pattern of the light source (an only semi-opaque film is sufficient but more than one film may be used). In practice, a light source induces dipoles in the reflector and in the director, mimicking the behavior of an optical Yagi-Uda antenna, which is commonly made of resonant metal nanoparticles (see for example J. Li et al., Phys. Rev. B 76, 245403 (2007), T. Kosako, et al., Nat. Photon. 4, 312 (2010), A. G. Curto, et al., Science 329, 930 (2010)). In the present invention instead, the passive reflector and director elements are thin films with appropriate optical properties, which will be described in what follows. Placing patch element in front of a reflector is known in antenna theory and design and have been proposed at optical wavelengths for enhancing OLEDs in combination with a grating structure (S. Mc Daniel et al. Opt. Express 18, 17477 (2010)), but without a director element (semi-opaque film, see below).

The reflector and/or the director may be layered, for example comprising a layer of Au, a layer of Ag and an intermediate layer of a dielectric material. In a more advanced embodiment, another element (optional) is added on top of the director and is here termed "metasurface" 103 (optional), shall play the role of an integrated flat lens (see e.g. A. V. Kildishev et al., Science 339, 1289 (2013) for a recent review). The metasurface 103 is for example a thin (thinner than the light wavelength) metal nanostructure that is able to steer an optical ray by a large amount in order to convert a wide radiation pattern into a narrow cone 108. Hence, a metasurface shall focus the emitted light further as a conventional lens. The lobe 106 is reflected and a single narrow lobe 108 is created, which may be efficiently collected by a fiber 107.

In case of a layered structure, with layers of different materials, an effective refractive index should be used instead of the refractive index.

A fluidic sample 110, 111 may flow in the spacer medium 109 to carry for example an analyte whose presence may be sensed via fluorescence detection, enhanced by the proposed device.

Figure 4:
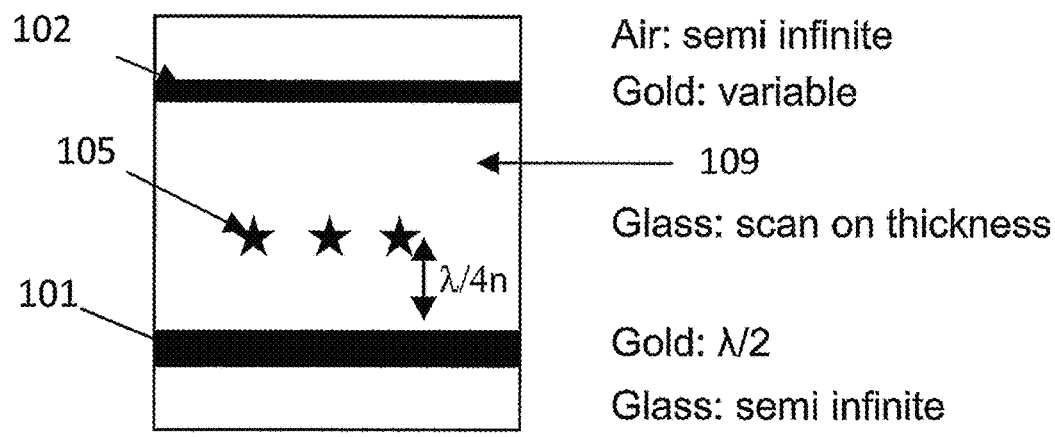
FIG. 4 shows the structure of an embodiment of the present invention.
Figure 5:
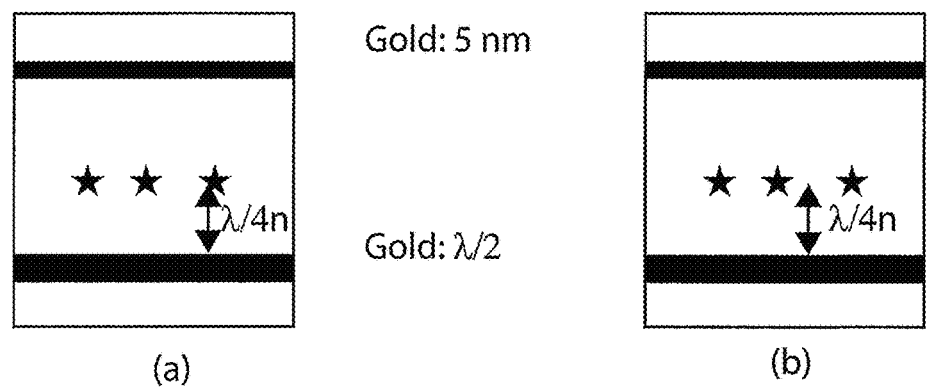
FIG. 5 shows two embodiments (a) and (b) of the present invention, where the relevant distance required to achieve beaming is indicated.

There has been both numerical study and experimental work to test the above basic technical idea. FIGS. 4 and 5 show the first numerical test we have made to design a planar optical device to channel light emitted by a sub wavelength source. We fixed the wavelength to 785 nm, which corresponds to the peak emission wavelength of DBT (a highly photo-stable dye that we decide to use for our experiments). The inventors have found that the chosen wavelength does not affect the design concept, but only the parameters (e.g. thickness of the layers, refractive index). The source is placed at a distance $\lambda/(4n)$ from a gold mirror, wherein $\lambda$ is here 785 nm and n=1.5 is the refractive index of the medium where the emitter sits. In general, the distances for which experiments have been carried out by the Inventors ranged from 25 nm to 450 nm.

Figure 8:
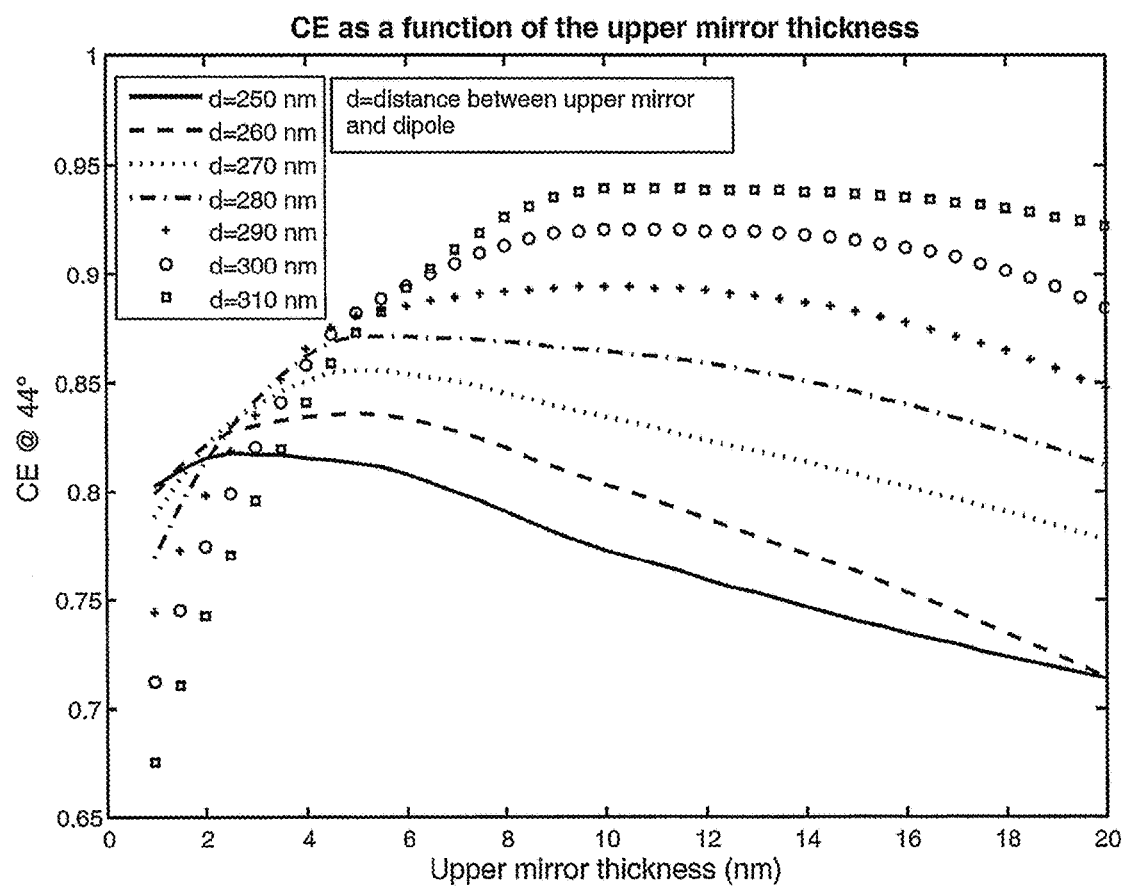
FIG. 8 shows a graph wherein the collection efficiency of the invention device at 44 deg. collection angle is plotted as a function of the thin film thickness of the thin film of the invention for a range of dielectric spacers of the invention between the light emitter and the reflector/mirror.

This distance has been tested to find the narrowest emission pattern in the upper hemisphere (see FIG. 8). The thickness of the mirror 101 is $\lambda/2$, but this value is just taken to ensure that the effect of the metal thickness is negligible. Then, a thin metal film 102 is placed on top of the dielectric spacer and the distance from the source is varied in order to investigate the radiation pattern. Under appropriate conditions, the thin film acts as a director that boosts the emission in the forward direction and narrows the radiation pattern.

In order to compare the performances of the case with and without thin film 102 (director), the inventors have performed simulations for both cases and also studied the dependence of the radiation pattern as a function of the spacer thickness 109 and the thin film thickness 102. The latter was varied from 50 nm to 1 nm. The optimal distance between the light source and the director, for each considered film thickness is listed in table 1. There, the light source is always kept at a separation of $\lambda/(4n)$ from the reflector. It is to be remarked that the choice of the upper semi-infinite medium has little effect on the radiation pattern. However, a finite glass layer without thin metal film would give performances lower than the case with semi-infinite glass or air.

TABLE 1

| Mirror thickness | Optimal distance |
|---|---|
| 40 nm | 340 nm |
| 20 nm | 330 nm |
| 10 nm | 310 nm |
| 5 nm | 300 nm |
| 2.5 nm | 260 nm |
| 1 nm | 250 nm |

Furthermore, the Inventors have found that larger thicknesses are not favorable, because of the increasingly reduced transparency of the thin film. On the other hand, very thin layers have little effect on the radiation pattern, as shown on FIGS. 6 and 7. Nonetheless, even a few nm of gold are not negligible.

Therefore, beside a best working distance for the source from the thin film (director, formed by continuous layer(s) of homogeneous material), there is also an optimal thickness for it, which depends on wavelength and on the other structure parameters. This shows that there is a relationship between the reflectivity of the thin film and the thickness of the dielectric spacer that has to be employed in order to beam the radiation pattern. To clarify this, FIG. 16 displays the transmission spectrum of the device with reflector and director as a function of the above mentioned parameters. It is found that the beaming at $\lambda$785 nm is related to the antenna resonance $\lambda_{res}$, which is given by the condition:

$$m\lambda_{res}=2nL+(\lambda_{res}/2\pi)(\psi 1+\psi 2) \quad (2)$$

Figure 15A:
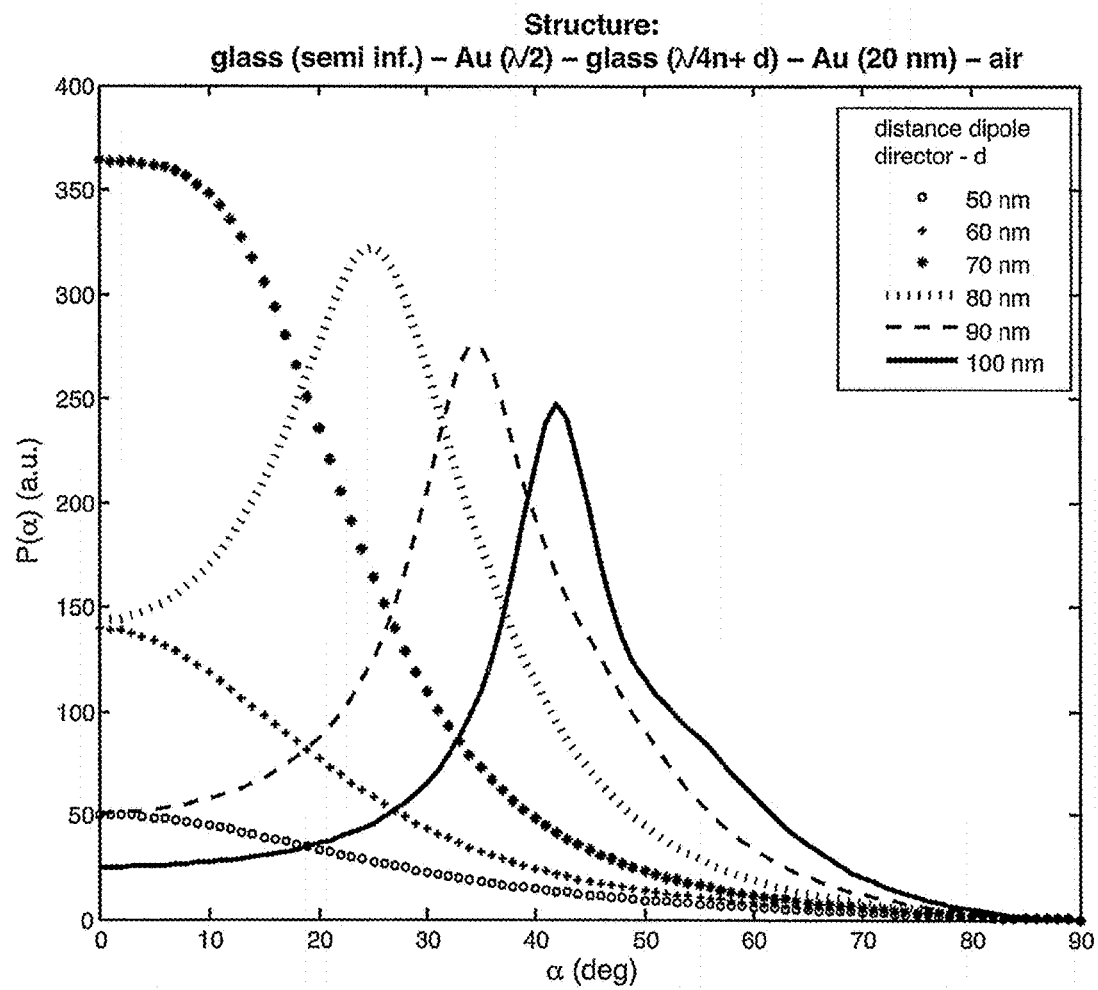
FIGS. 15a and 15b show in (a) a graph with the radiation pattern for the invention embodiments with reflector and director (20 nm thick gold film) for other values of the spacer between reflector and director, and in (b) the case wherein the emission wavelength is in resonance with the optical system of the invention. The radiation pattern shows no beaming irrespective of the position of the light source in the spacer medium (no beaming)
Figure 15B:
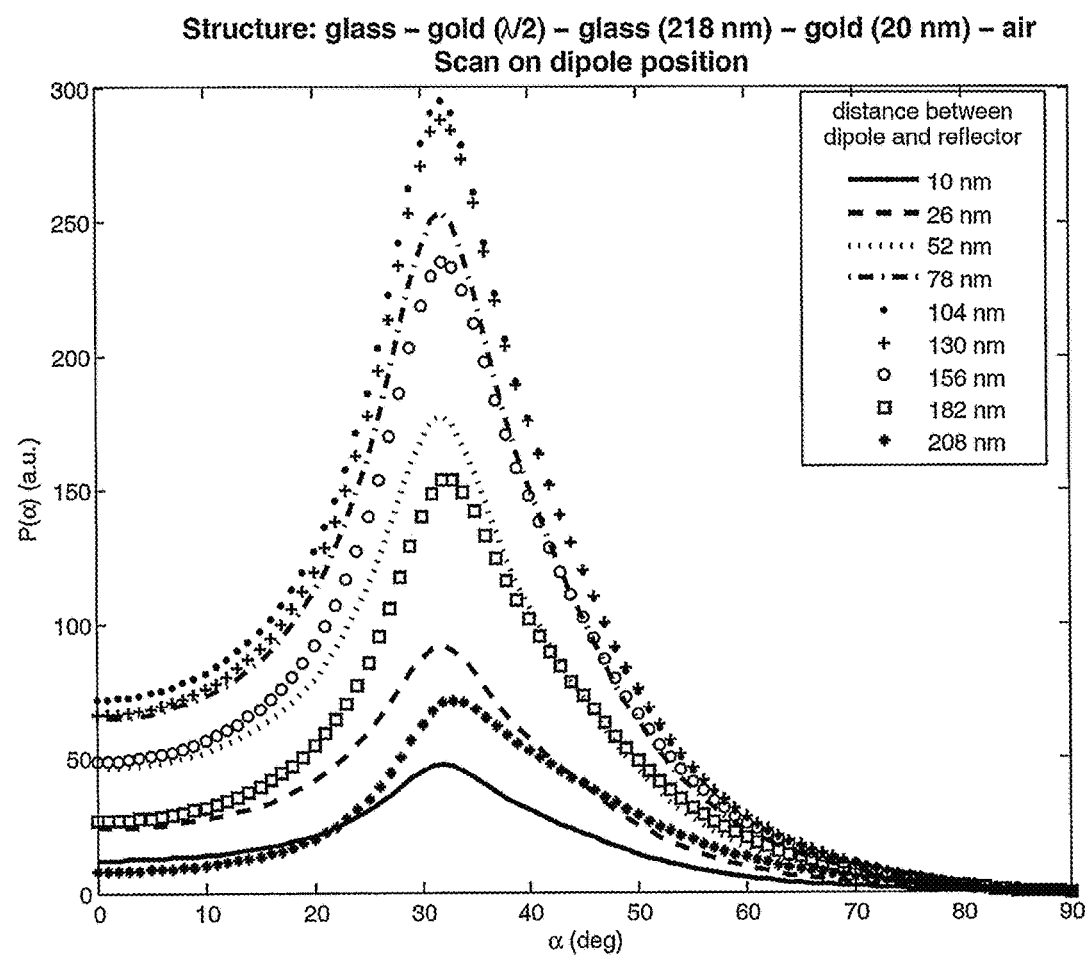
Figure 16:
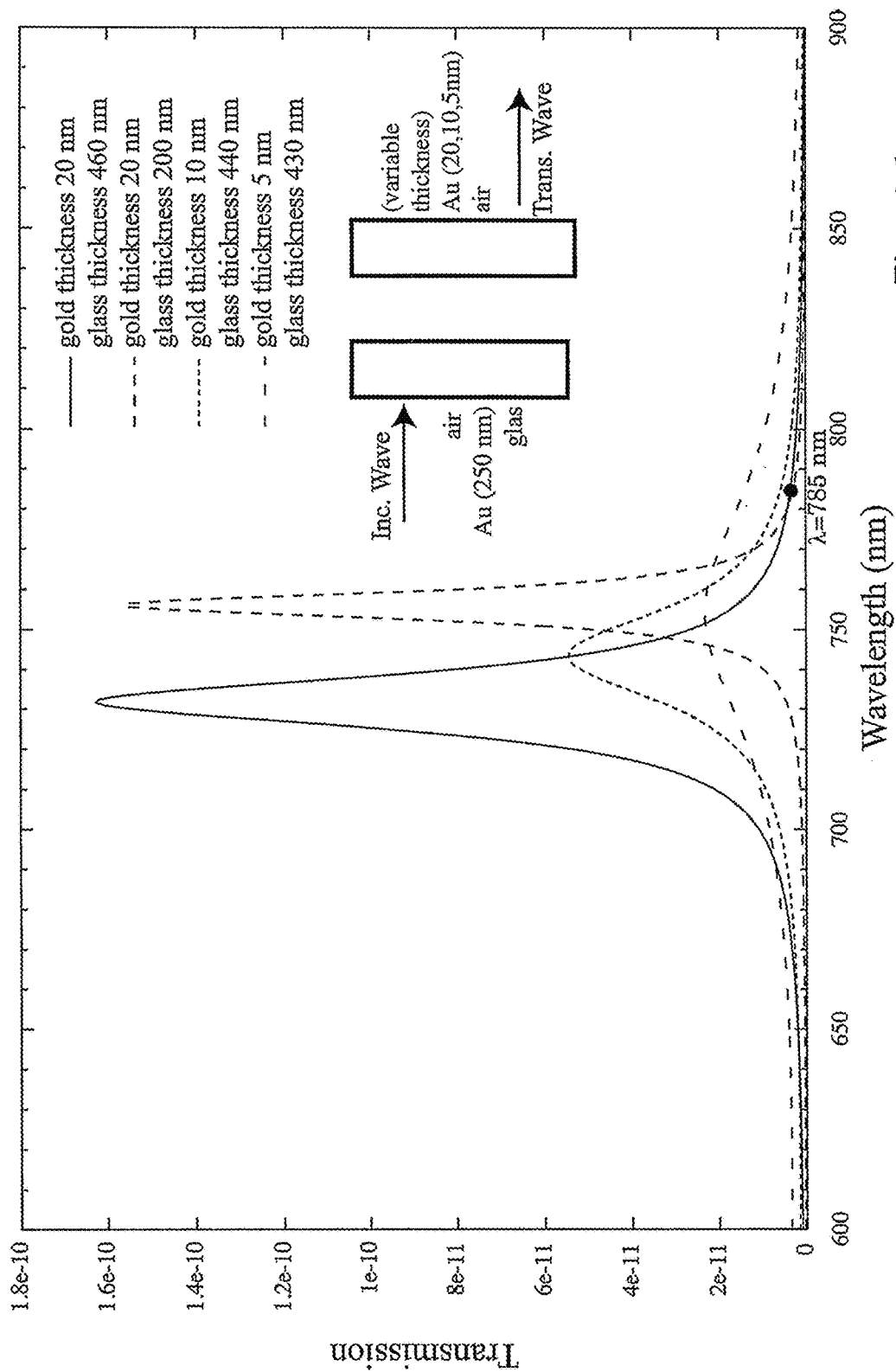
FIG. 16 shows a graph with the transmission spectrum for two layered structures made of air, 250 nm thick gold film, glass spacer of variable thickness, a gold thin film of variable thickness, air. These correspond to the embodiments with reflector and director that show the best beam forming in FIGS. 6 and 15a and in table 1.
Figure 17A:
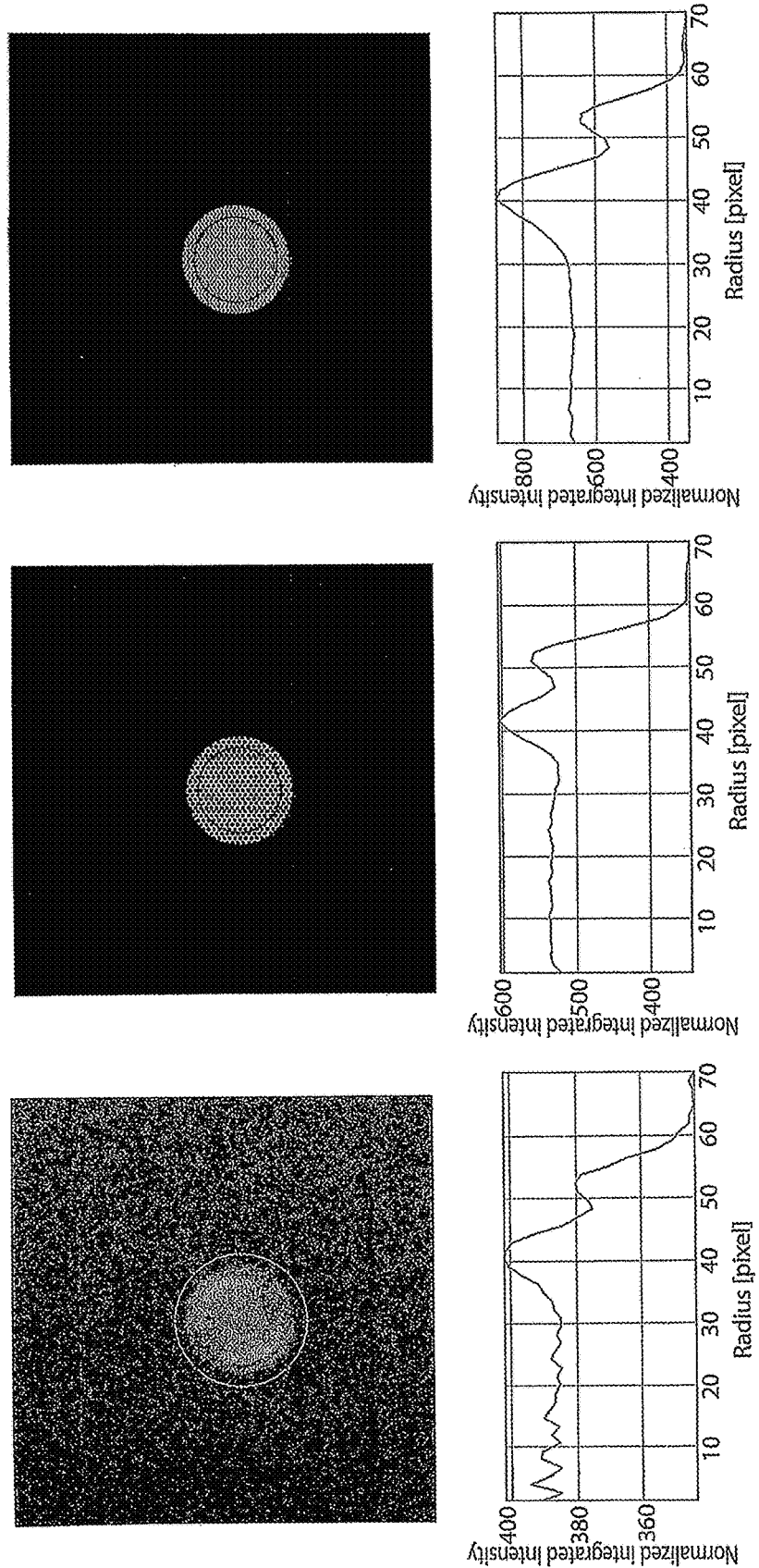
FIGS. 17A and 17B show the measured fluorescence signal from Dybenzoterrylene (DBT) molecules in anthracene deposited on a glass cover slip (a) and on a Polyvinyl alcol (PVA) spacer of thickness 70 nm spin coated on an anthracene thin film containing DBT molecules followed by the evaporation of a gold mirror on PVA (b). The images acquired by an electron-multiplying charge-coupling device (EMCCD) represent the emission pattern and the curves below each image is a cross sectional cut, showing the improvement in the collected signal and beam forming.
Figure 17B:
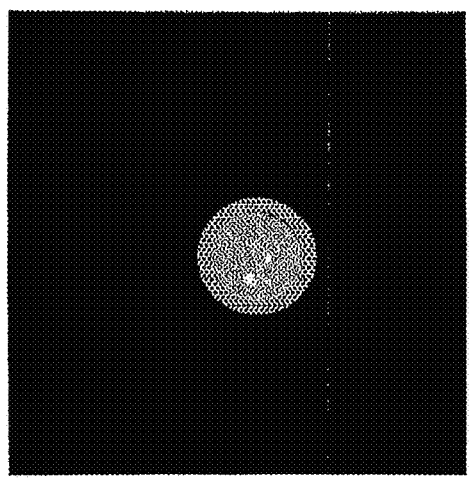
Figure 17B:
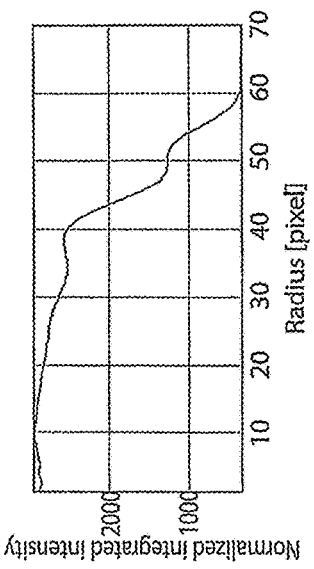
Figure 17B:
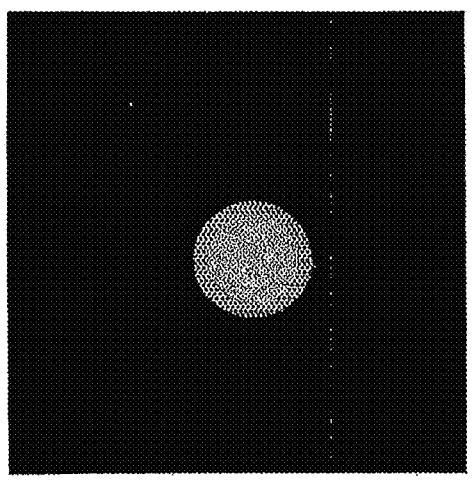
Figure 17B:
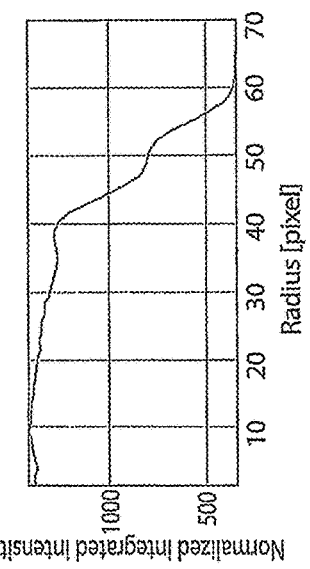
Figure 17B:
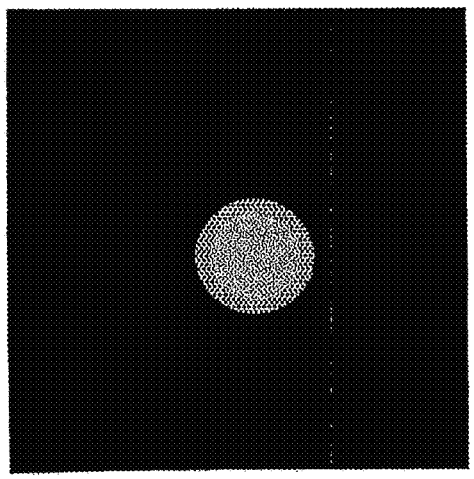
Figure 17B:
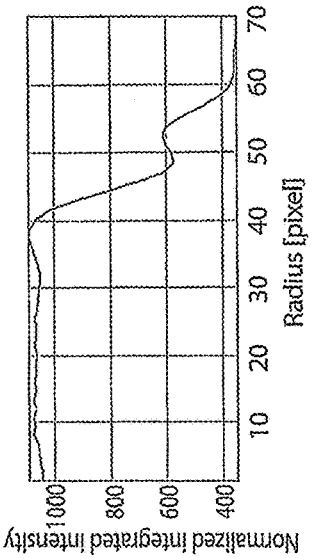

Here, m is an integer, L is the distance between reflector and director, and $\psi 1$ and $\psi 2$ are the phase shifts of a reflected wave on reflector and director, respectively. Two ideal mirrors would exhibit $\psi 1=\psi 2=\pi$. Changing the thickness of the director affects $\psi 2$ and consequently L in order to keep the position of the resonance constant. In practice, however, the beam forming is not due to an on-resonance effect like in a micro cavity, since the operating wavelength is red-shifted with respect to the antenna resonance. The Inventors have found that the optimal distance between reflector and director (between the respective facing surfaces) ranges between $\lambda/(2.9n)$ and $\lambda/(2.5n)$ (see FIG. 15(a)), and between $\lambda/(1.3n)$ and $\lambda/(1.1n)$ (see FIG. 6 and Table 1), depending on the thickness of the director. An explanation for the two different ranges of parameters can be inferred from Eq. (2). In fact, these can be related to the resonance conditions $L=\lambda_{res}/(2n)$ and $L=\lambda_{res}/n$ that would be given by Eq. (2) if reflector and director were ideal mirrors for m equal to 2 and 3, respectively. Note however that in the present Invention $\lambda_{res}$ is slightly different due to the fact that director and reflector are not ideal mirrors and, importantly, that $\lambda$ must be redshifted with respect to $\lambda_{res}$, as shown in FIG. 16. It has been verified by the Inventors that at $\lambda=\lambda_{res}$ there is no beamforming, irrespective of the position of the light source in the spacer medium, as shown in FIG. 15(b)).

Figure 6:
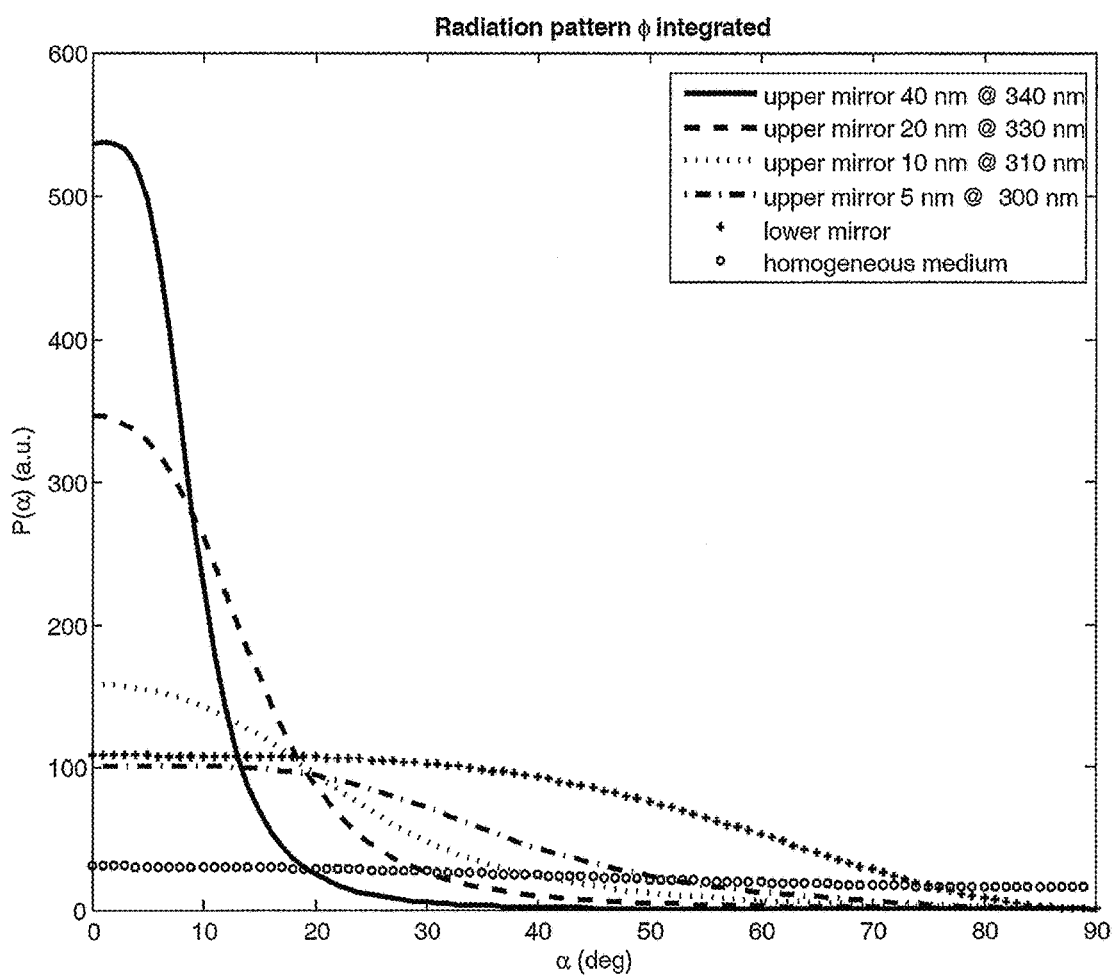
FIG. 6 shows a graph with the radiation pattern for the best parameter values for several invention embodiments (with reflector and director, with reflector only) and compares them to the case of emission in free space (homogeneous medium)

The graph of FIG. 6 shows the radiation pattern for the best parameter values of the embodiment reflector+director and compares it with the case of one gold mirror 101 and in free space (without the director). The difference is remarkable, especially for the case where the director is 20 nm thick. Note that for the 20 nm thin film the power is almost within a cone with a semi-angle of 20 degrees. Analogous performances are found for the same director with a spacer of about $\lambda/(4n)+70$ nm, which can be explained by Eq. (2) and the fact that for a 20 nm thick gold film $\psi 2$ is not equal to $\pi$. We observe that reasonable values for the thickness of a gold director for $\lambda$ around 785 nm should be between 10 and 30 nm. Outside this range either the directivity or the total radiated power are reduced.

Figure 7:
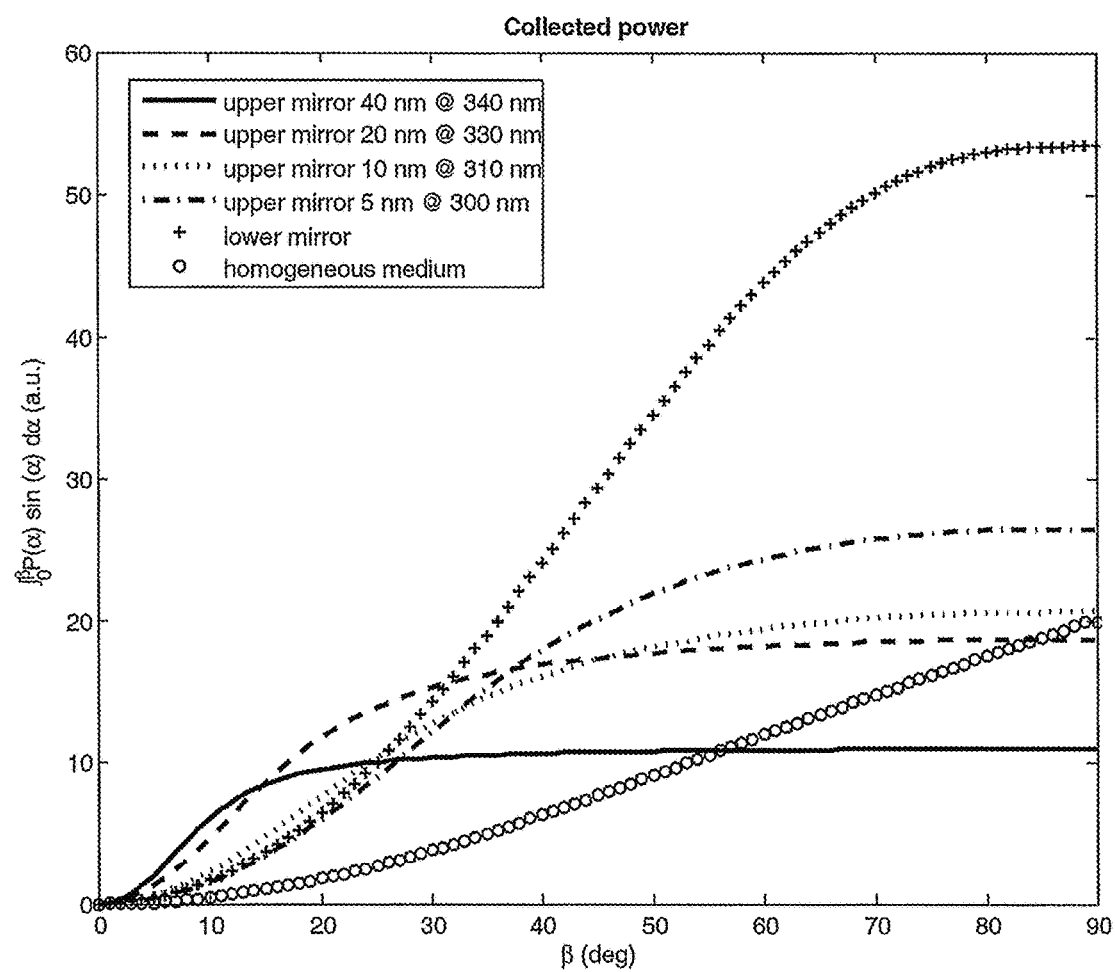
FIG. 7 shows the result of integration of the curves of FIG. 5 up to various collection angles.

To verify to what extent is the gain in terms of amount of collected light, the above curves have been integrated up to various collection angles. The result is shown in FIG. 7, wherein the advantage of the invention structure is evident for collection angles smaller than 30 degrees, with the largest enhancement at about 15-20 degrees. Note that the upper mirror (director) remarkably improves the result.

It should be mentioned that for very large collection angles there is no advantage in placing the thin metal film (director), because there is always some energy absorbed in the metal. Therefore, if one could ideally collect up to 90 degrees, it would be better not to use any thin film on top of the light source, as shown by the collected data (because the director reduces the transmitted power for no benefit on the collection).

It has been analyzed by the Inventors how the device is sensitive to certain parameters, such as the thickness of the thin film (director) and of the spacer medium (a spacer which can be dielectric or not). The results are shown in FIGS. 8 and 9.

In FIG. 8, the collection efficiency at 44 deg. collection angle is plotted as a function of the thin film thickness for a range of dielectric spacers. Note that, although there is a variation in the performances, especially for the thinner films, the data are quite robust considering the tolerance that can be achieved by state-of-the-art nano fabrication methods.

Figure 9:
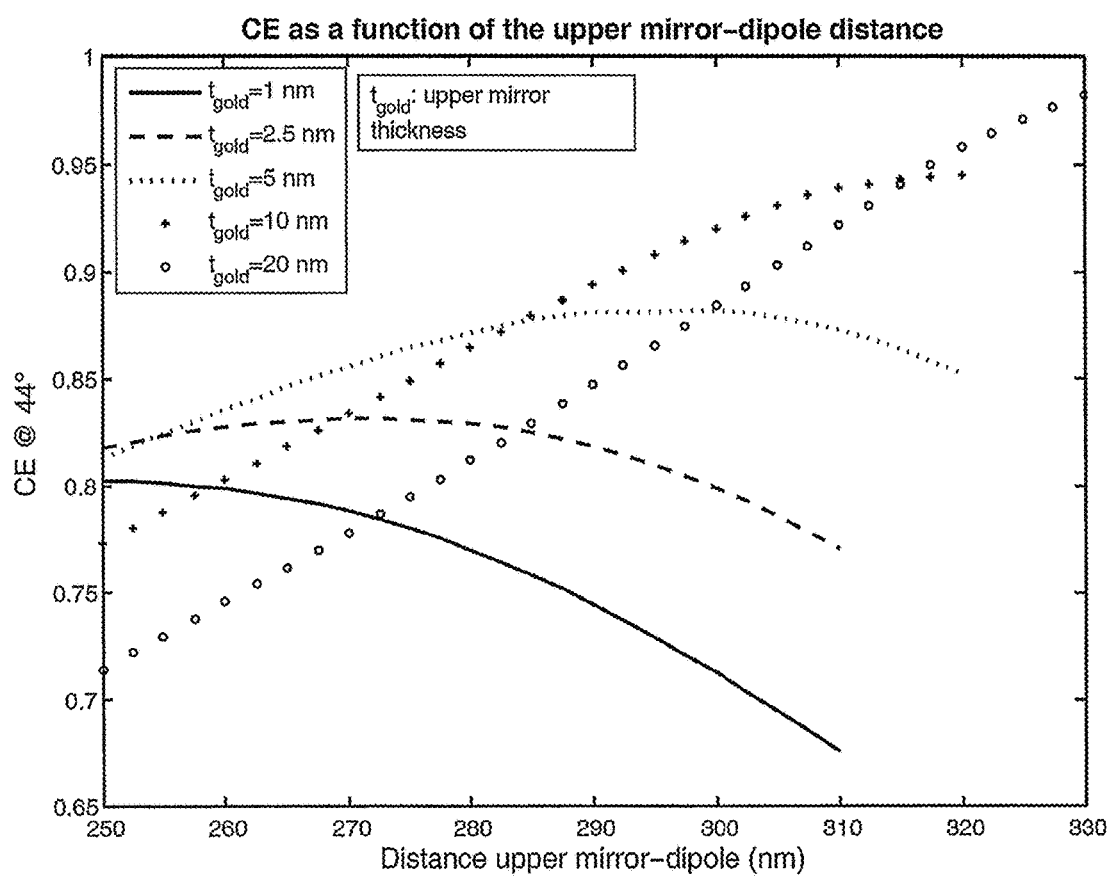
FIG. 9 shows the same data of FIG. 8 but displayed as a function of the dielectric spacer for different thin film thicknesses.

In FIG. 9, the same data are displayed as a function of the dielectric spacer for different thin film thicknesses. The dependence on the dielectric spacer is more remarkable for thicker gold films, although the collection efficiency changes only by a few percent if the spacer varies its thickness by 10 nm. This dependence on thickness can be translated into dependence on wavelength. We can therefore state that the device performances are not affected if the wavelength bandwidth is within a few 10 s of nm.

Example 1

Figure 10:
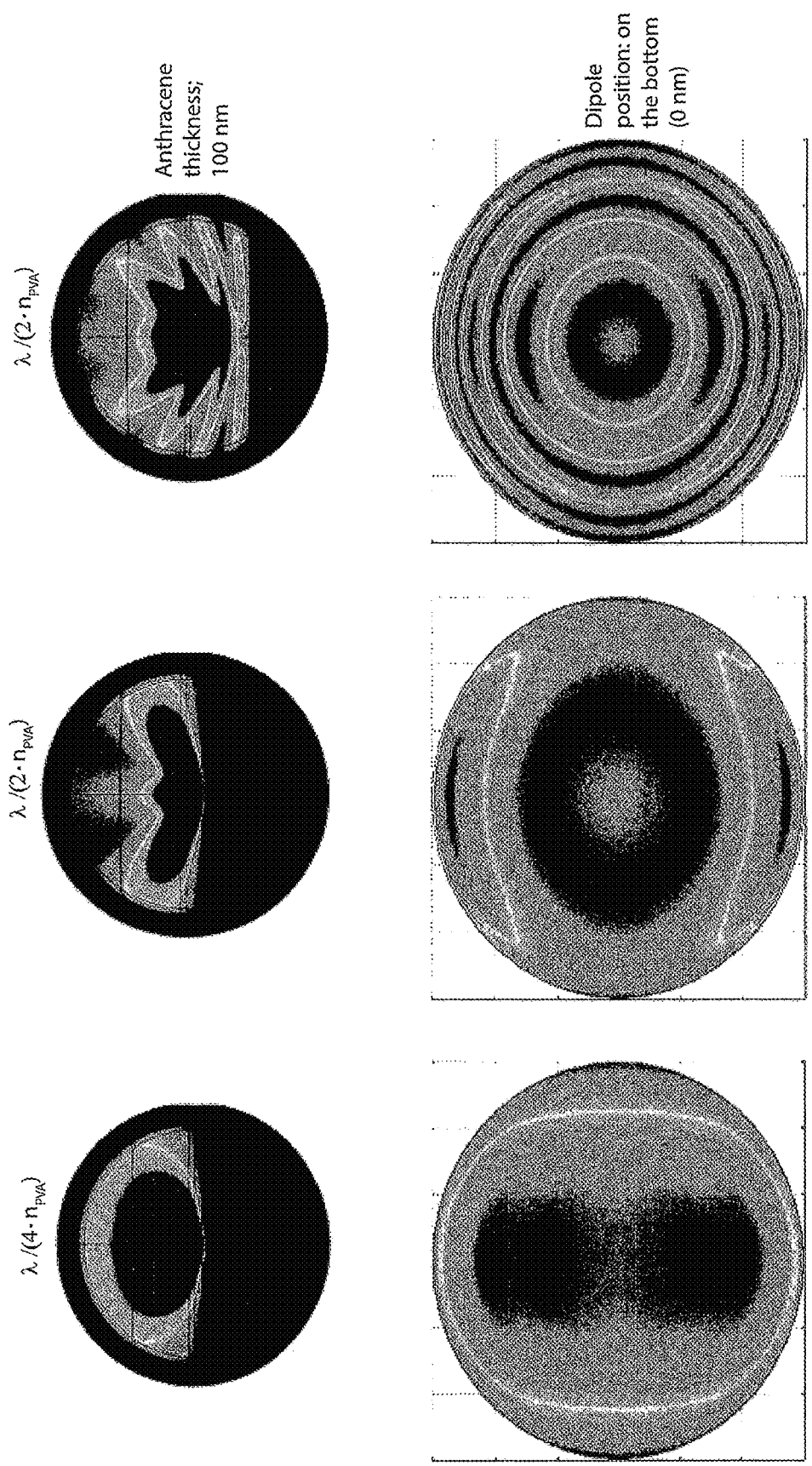
FIG. 10 shows the effect of beamforming with and without the invention structure regarding the embodiment with reflector only (the invention structure and parameters are the one giving the results of left column)

The Inventors have performed experiments to verify the above simulations. First, the case of a dipole in front of a metal mirror (reflector) and studied its radiation pattern as a function of distance from it has been considered. A thin layer of anthracene with DBT molecules has been spin coated on a cover glass, then a polymer film is spin coated to act as a dielectric spacer and finally a gold film is sputtered on the spacer to act as a mirror. In the first place the wish is to couple the device with a solid immersion lens to be able to measure the radiation pattern up to large angles. The simulation results are shown in FIG. 10, wherein $n_{PVA}$ is the refractive index of the utilized spacer. The distance from the mirror is relevant for determining the collection efficiency and a distance of $\lambda/(4n_{PVA})$ is the best case compared to the other two cases, where more than one lobe is found.

Example 2

Figure 11A:
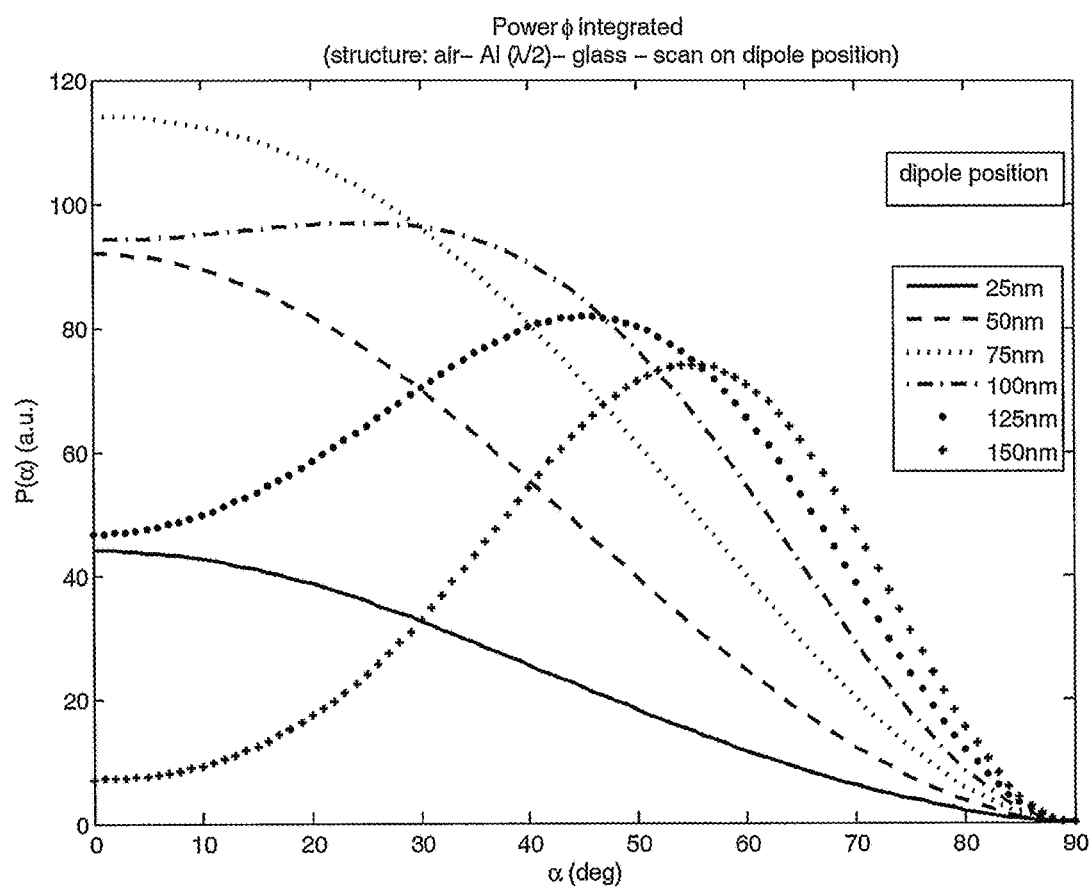
FIGS. 11a, 11b, and 11c show the profile of collection efficiency (on (c)) and emission profile (on (a) and (b)) in the case of an aluminum reflector and wavelength of 530 nm.
Figure 11B:
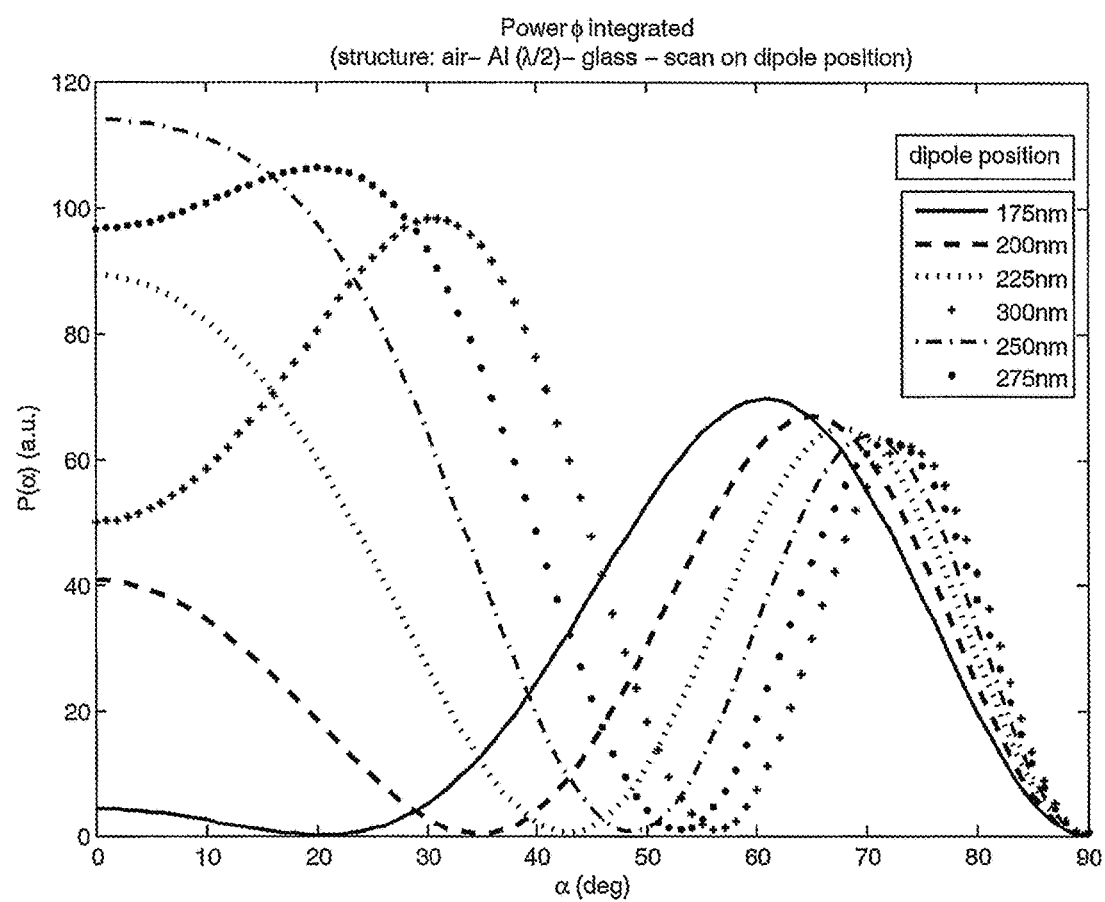
Figure 11C:
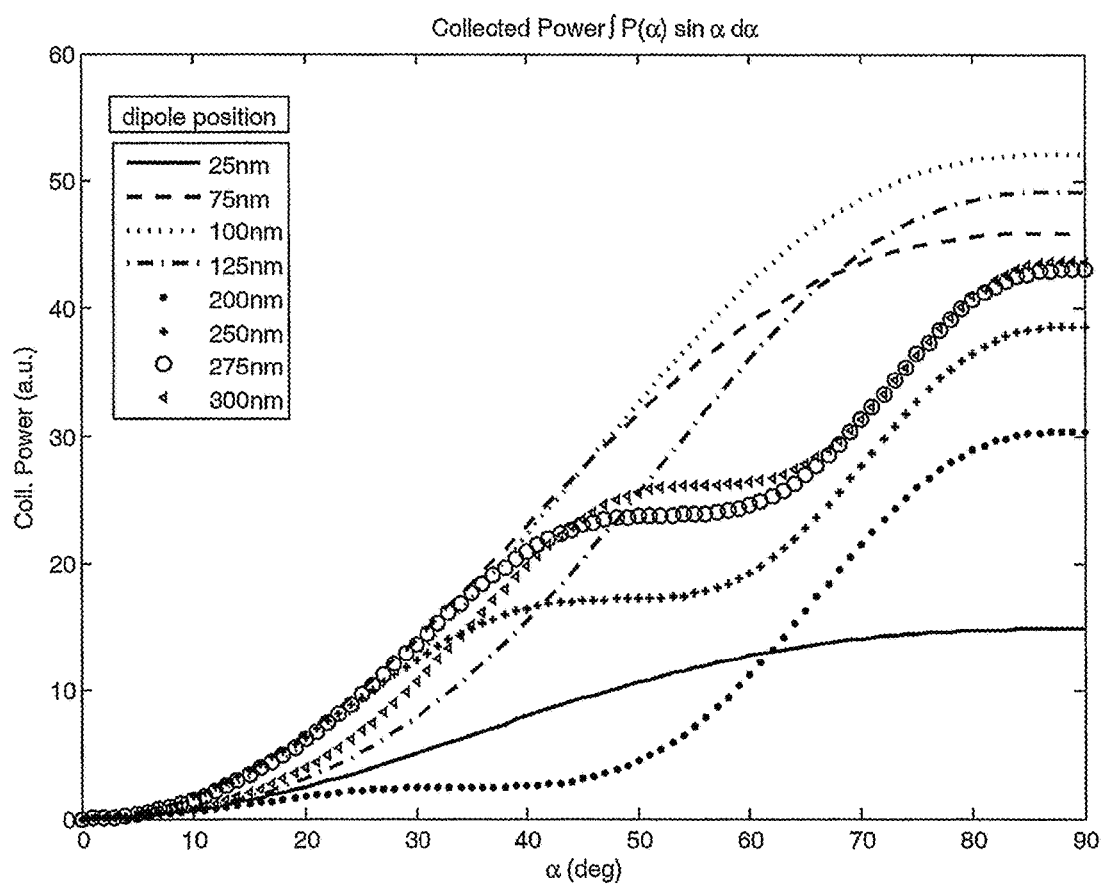

FIG. 11 shows the case of an aluminum reflector. The collection efficiency (on (c)) is in this case larger when the emission profile (on (a) and (b)) has only one central lobe. The wavelength corresponds to 530 nm. This corresponds to a spacer of about 75 nm, which is not equal to the value $\lambda/(4n)$ because the phase shift due to the reflector is not $\pi$ as for an ideal reflector. For larger distances, the appearance of lateral lobes (see (a) and (b)) reduces the collection efficiency, especially at small angles (see (c)). On the other hand, for shorter distances the emitter power is gradually quenched due to near-field energy transfer and cancellation of the dipole due to image charges (R. Chance et al., Adv. Chem. Phys. 37, 1 (1978)).

Example 3

Figure 12A:
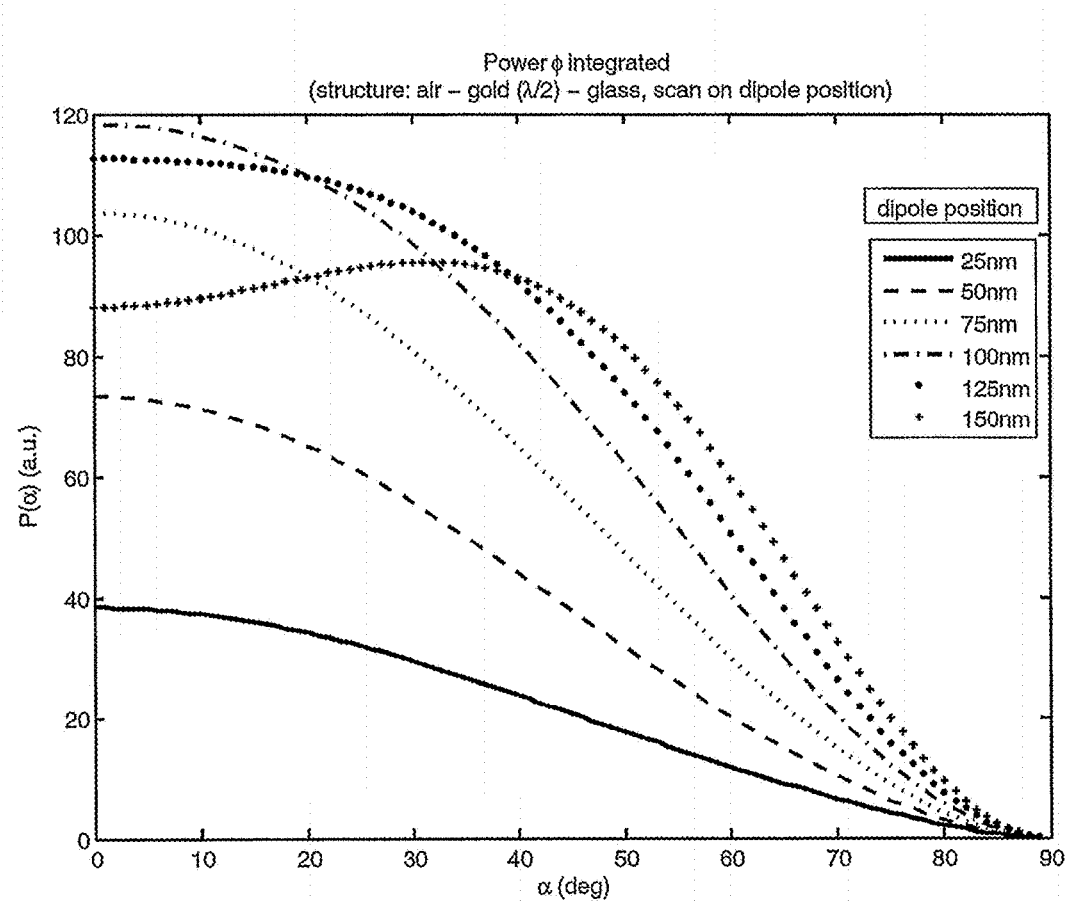
FIGS. 12a, 12b, and 12c show the profile of collection efficiency (on (c)) and emission profile (on (a) and (b)) in the case of a gold reflector and wavelength of 785 nm.
Figure 12B:
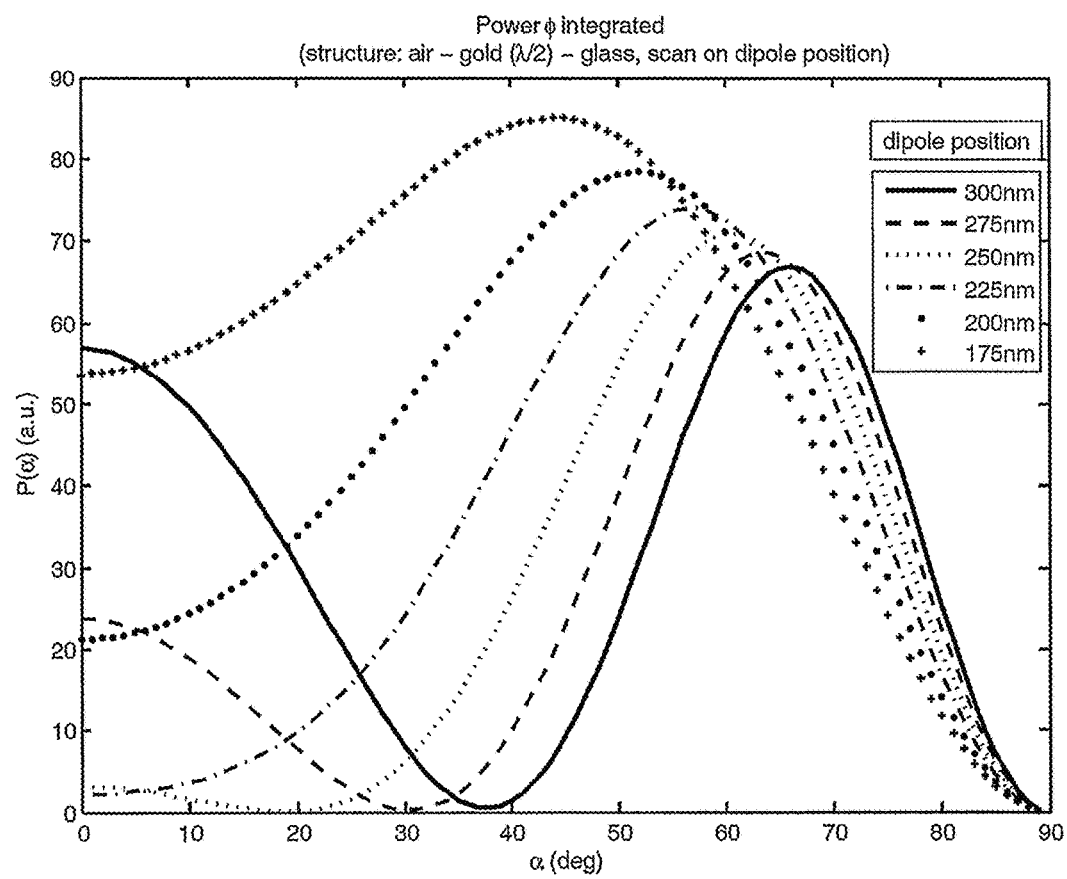
Figure 12C:
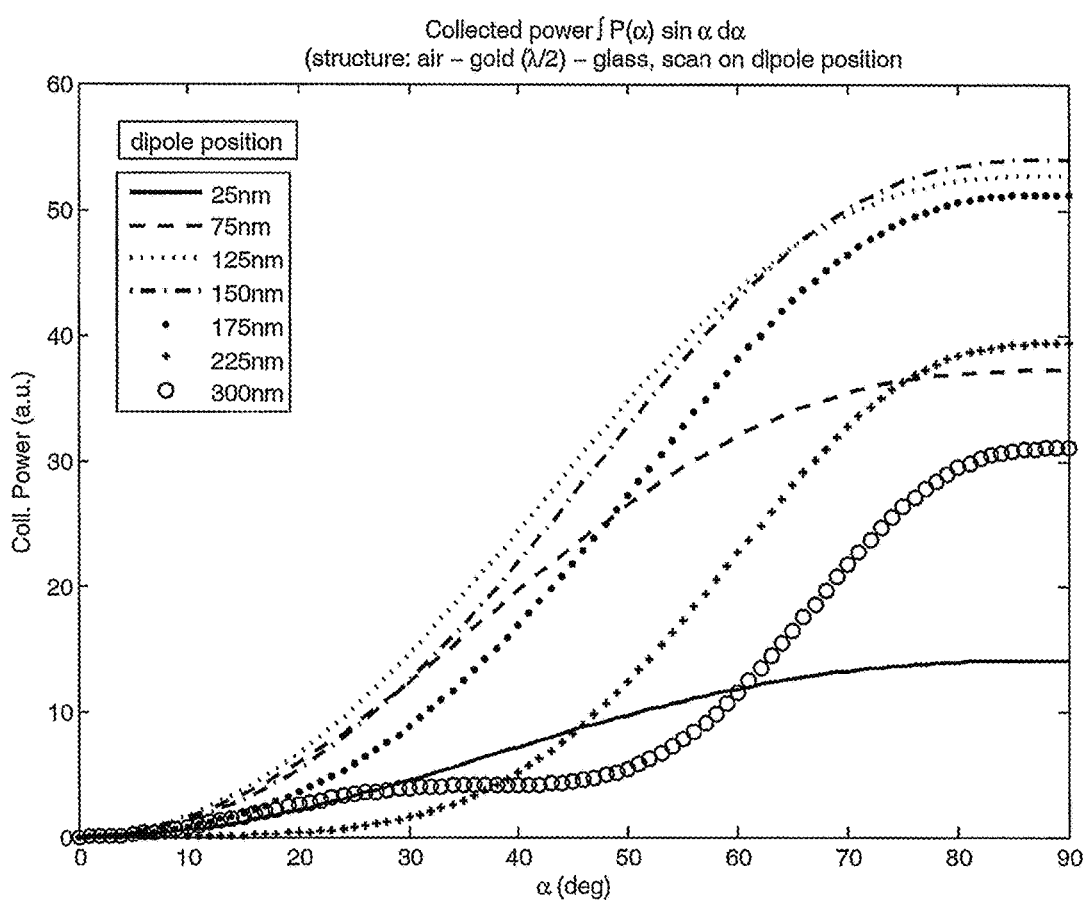

FIG. 12 shows the case of a gold reflector. The collection efficiency (on (c)) is in this case larger when the emission profile (on (a) and (b)) has an only central lobe. The wavelength corresponds to 785 nm. This corresponds to a spacer of about 125-150 nm, which is about the value $\lambda/(4n)=130$ nm, because the phase shift due to reflector is now closer to $\pi$, as for an ideal reflector. For larger distances, the appearance of lateral lobes (see (a) and (b)) reduces the collection efficiency, especially at small angles (see (c)). On the other hand, for shorter distances the emitter power is gradually quenched due to near-field energy transfer and cancellation of the dipole due to image charges (R. R. Chance et al., Adv. Chem. Phys. 37, 1 (1978)).

Example 4

Figure 13A:
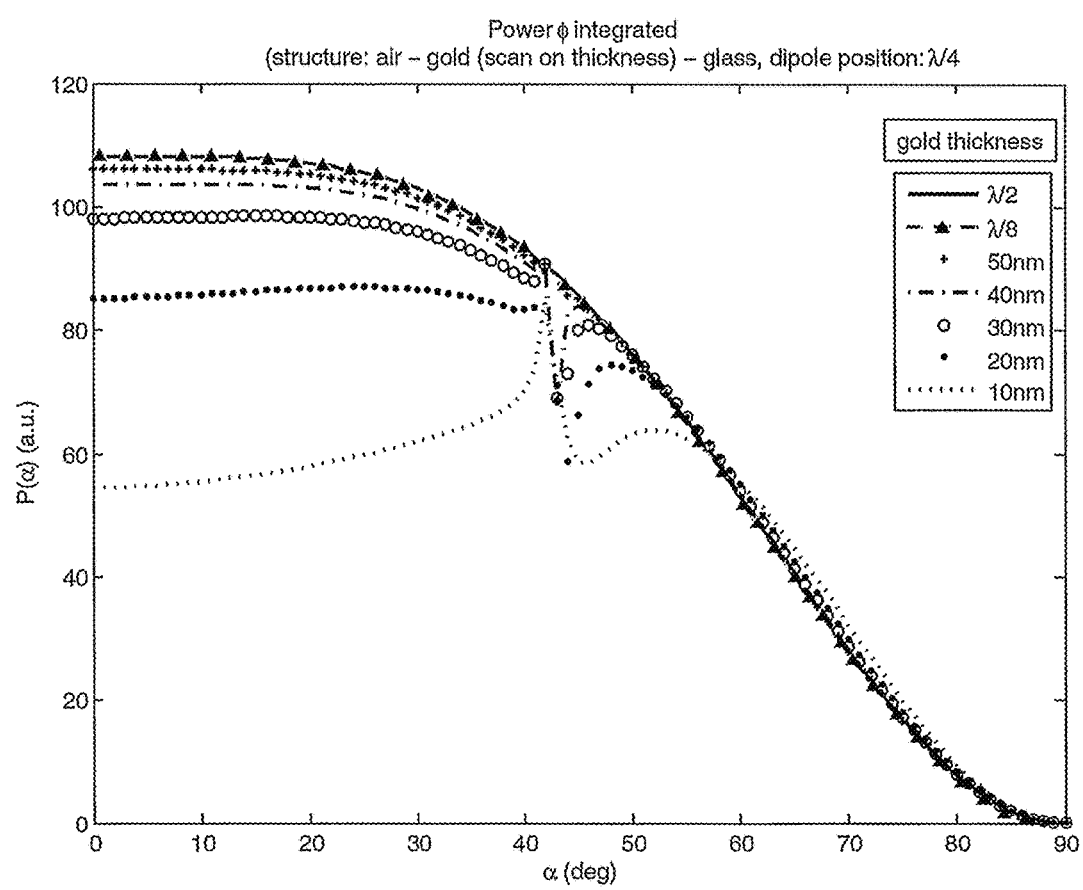
FIGS. 13a and 13b show the profile emission (a) and the collection efficiency (b) for several reflector thicknesses.
Figure 13B:
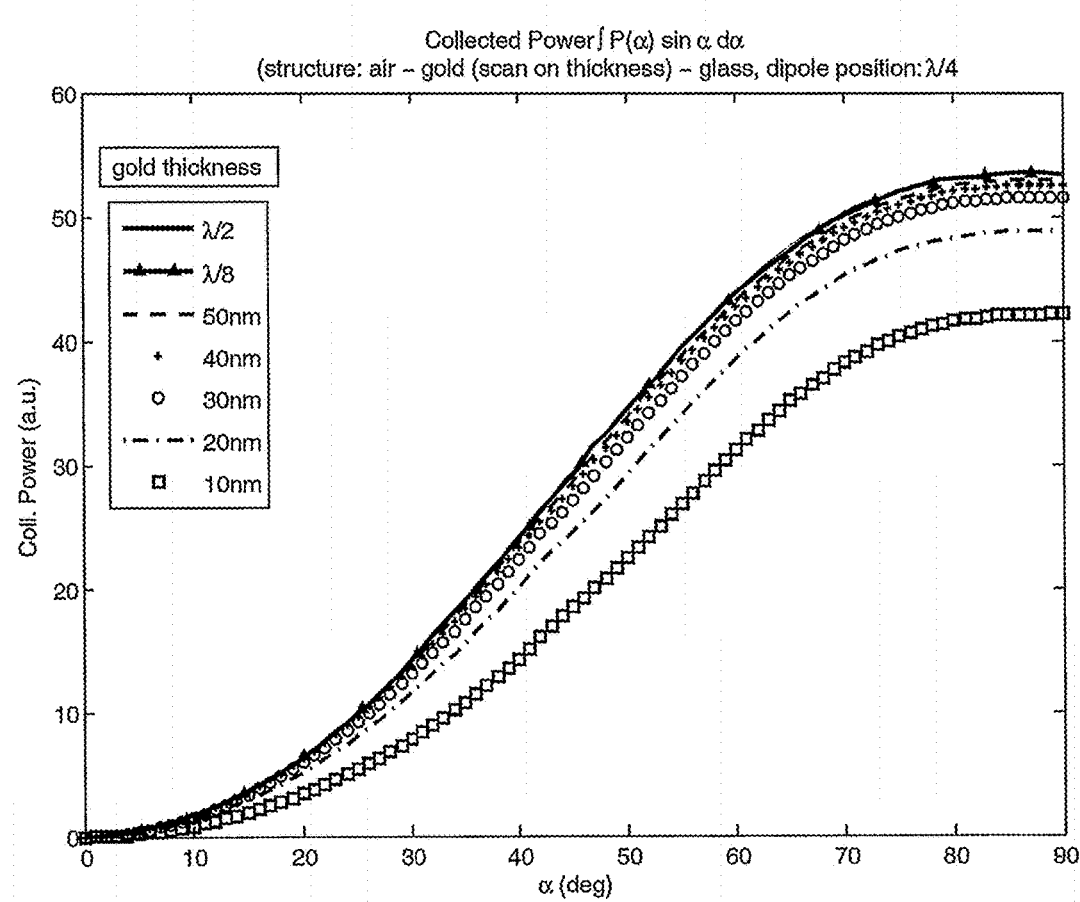

FIG. 13 shows the profile emission (a) and the collection efficiency (b) for several reflector thicknesses. By reducing the thickness of the reflector, the performances worsen when the reflectivity significantly decreases. In the latter case, the emission profile is not constituted by a single central lobe any longer. The peak at 40 degrees corresponds to the excitation of the surface plasmon of the metal film.

Figure 14:
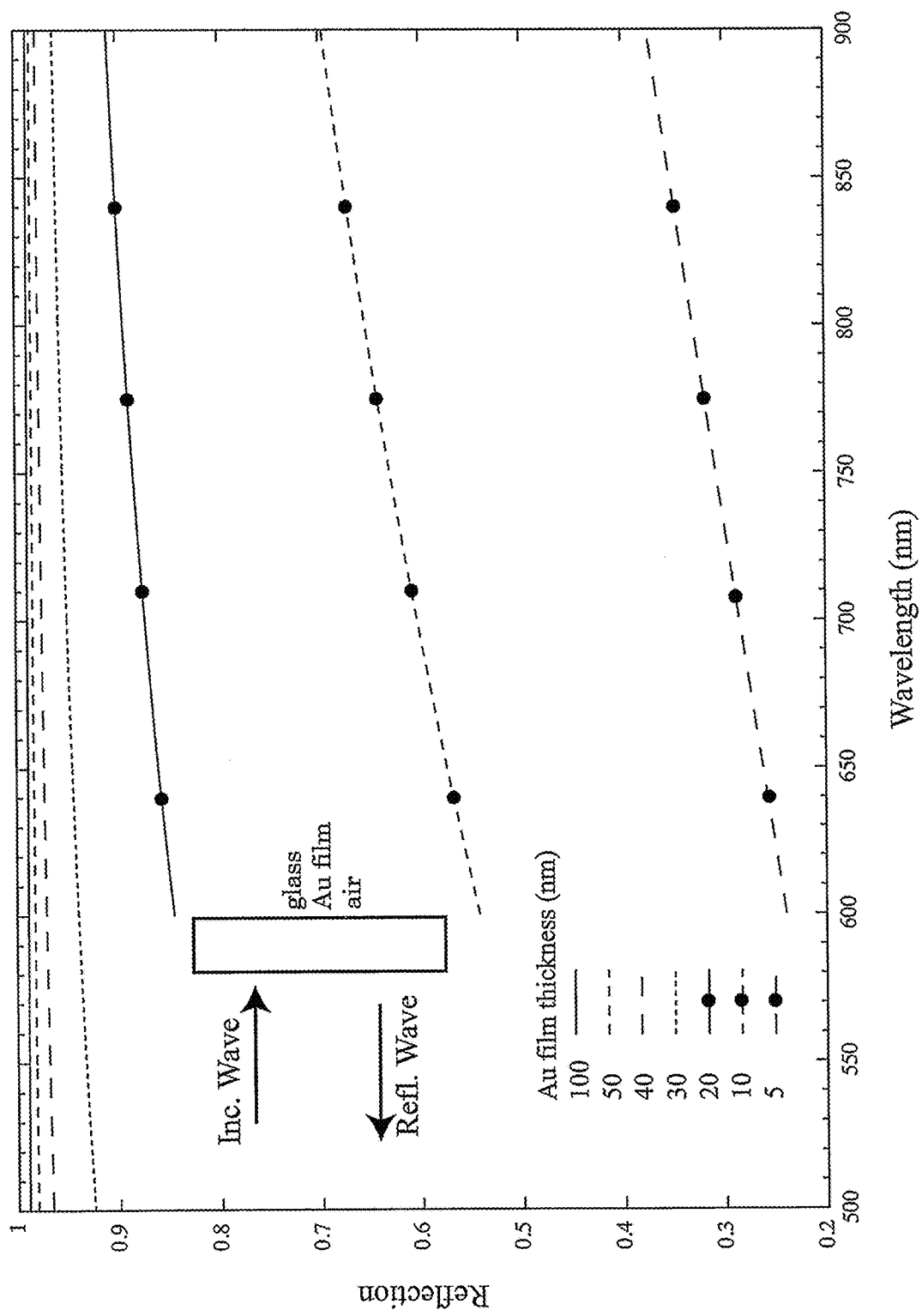
FIG. 14 shows the reflectivity of the reflector as a function of the incident wavelength for different thicknesses of a gold film; by correlating the graph to FIGS. 13a and 13b, one derives that the reflectivity must be high (>80-90%) in order to obtain the beamforming.

FIG. 14 shows the reflectivity as a function of the incident wavelength for different thicknesses of a gold film. By correlating the graph to FIG. 13, one derives that the reflectivity must be high (>80-90%) in order to obtain the beam forming. Furthermore, by correlating the graph to FIGS. 6 and 7 and referring to the reflectivity of the director, one infers that also the reflectivity of the director must be at least 50% to have an appreciable effect on beam forming, with the best results obtained for reflectivity above 80%.

Example 5

FIG. 17 shows the radiation pattern acquired with an EMCCD camera by the technique of back-focal-plane (BFP) imaging. FIG. 17 (*a*) is the reference signal, corresponding of a sample made of DBT molecules in an anthracene thin film spin coated on a glass cover slide. FIG. 17 (*b*) is our device, whereby the anthracene film is at a distance of 70 nm from a gold film. The improvement in terms of collected signal is remarkable and reproducible over many samples (only 3 have been shown for example).

Example 6

Figure 19:
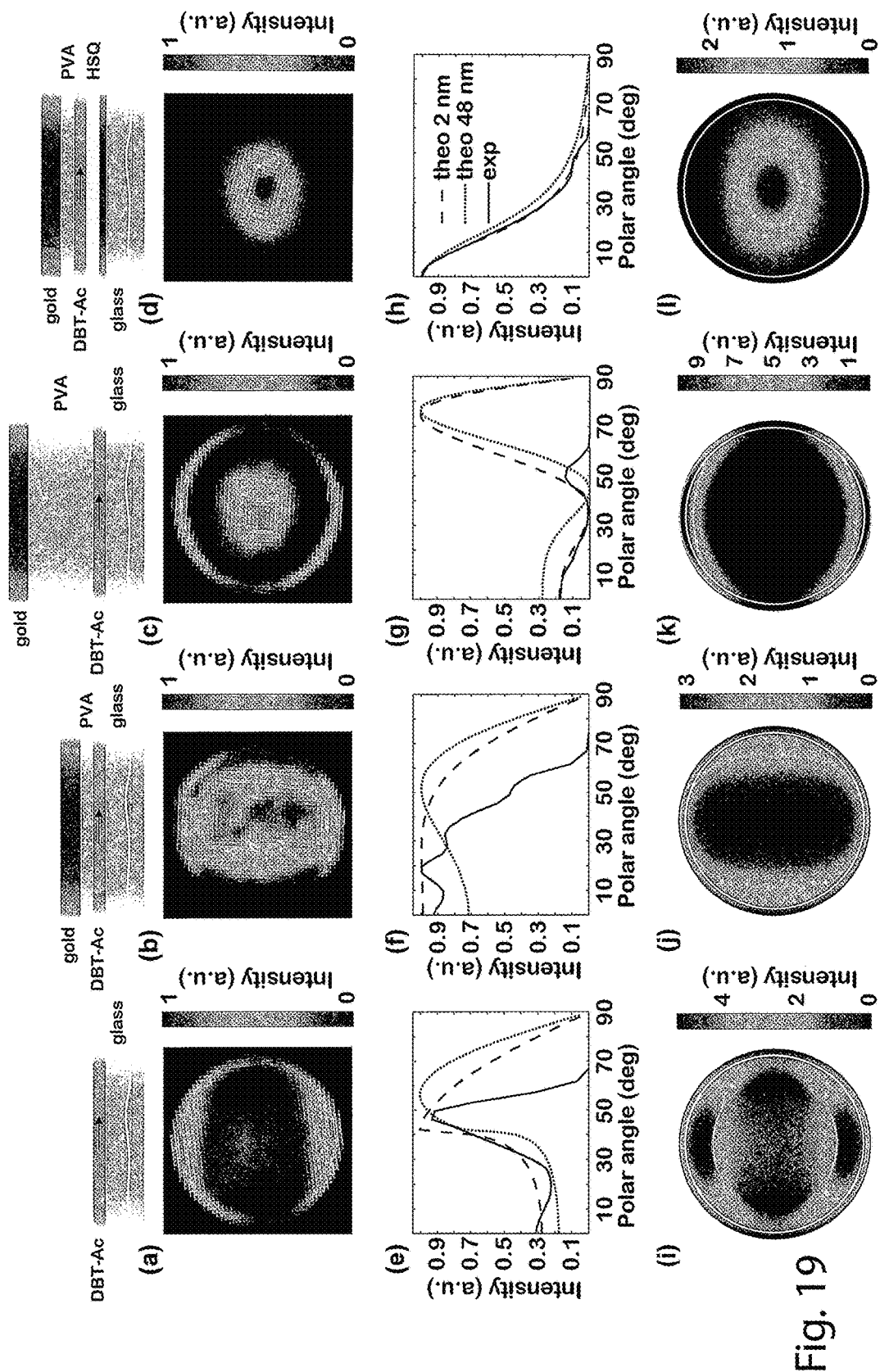
FIG. 19 shows in (a)-(d) a sketch of the samples and corresponding Back Focal Plane (BFP) images of a single DBT molecule acquired with an EMCCD camera. (e)-(h) Comparison between calculated emission patterns for $\lambda=785$ nm and cross-cuts of the experimental BFP images. The shaded areas represent the objective transfer function, from 0 transmission (gray) to 1 (white). The two theoretical curves for each case correspond to different positions of the DBT molecule in a 50 nm thick Anthracene (Ac) film: 2 nm from the top (dashed curve) and 2 nm from the bottom (dotted curve) interface. (i)-(l) Theoretical BFP images that reproduce the experimental results. The plots are normalized with respect to the maximum value of the radiation pattern of a Hertzian dipole in a homogeneous medium with n=1.5. The white circles show the nominal NA of the collection optics ($\theta=67$). (a), (e), (i) Experimental reference case with glass cover slip ($n_{glass}=1.52$), 50 nm DBT-Ac ($n_{Ac}=1.6$) and air ($n_{air}=1$); (b), (f) (j) System with reflector, composed by a semi-infinite glass cover slip, 50 nm DBT-Ac, 70 nm PVA ($n_{PVA}=1.49$), 100 nm gold and air; (c), (g), (k) Same as before, but with PVA of thickness 300 nm; (d), (h), (l) System with director and reflector, composed by a semi-infinite glass cover slip, 20 nm gold, 50 nm Hydrogensylsesquioxane (HSQ) ($n_{HSQ}=1.4$), 50 nm DBT-Ac, 70 nm PVA, 100 nm gold and air.

FIG. 19 is (a)-(d) are a sketch of the samples and corresponding BFP images of a single DBT molecule acquired with an EMCCD camera. (e)-(h) Comparison between calculated emission patterns for $\lambda=785$ nm and cross-cuts of the experimental BFP images. The shaded areas represent the objective transfer function, from 0 transmission (gray) to 1 (white). The two theoretical curves for each case correspond to different positions of the DBT molecule in a 50 nm thick Ac film: 2 nm from the top (dashed curve) and 2 nm from the bottom (dotted curve) interface. (i)-(l) Theoretical BFP images that reproduce the experimental results. The plots are normalized with respect to the maximum value of the radiation pattern of a Hertzian dipole in a homogeneous medium with n=1.5. The white circles show the nominal NA of the collection optics (θ=67). (a), (e), (i) Experimental reference case with glass cover slip ($n_{glass}$=1.52), 50 nm DBT-Ac ($n_{Ac}$=1.6) and air ($n_{air}$=1); (b), (f) (j) System with reflector, composed by a semi-infinite glass cover slip, 50 nm DBT-Ac, 70 nm PVA ($n_{PVA}$=1.49), 100 nm gold and air; (c), (g), (k) Same as before, but with PVA of thickness 300 nm; (d), (h), (l) System with director and reflector, composed by a semi-infinite glass cover slip, 20 nm gold, 50 nm HSQ ($n_{HSQ}$=1.4), 50 nm DBT-Ac, 70 nm PVA, 100 nm gold and air.

Figure 2:
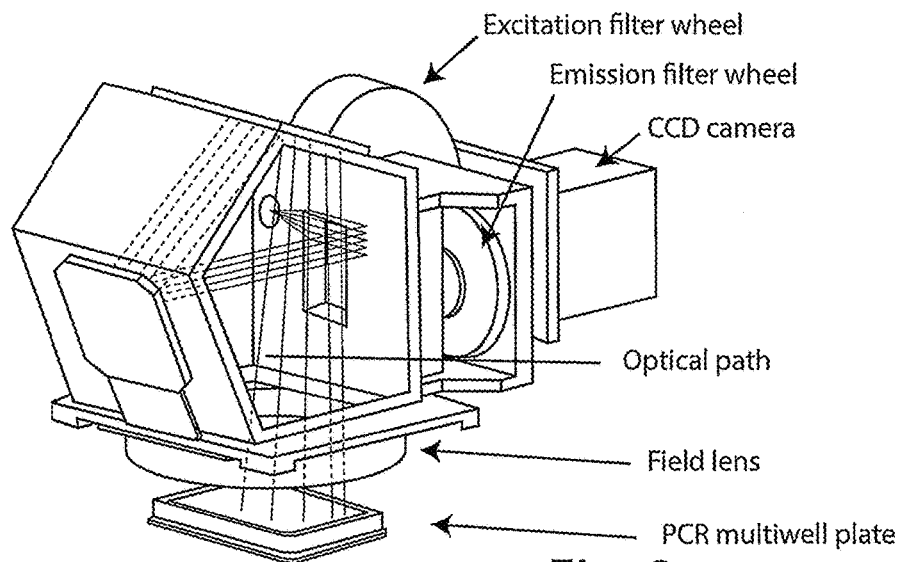
FIG. 2 shows a schematic overview of the LightCycler® 480 Instrument's detection unit, according to the prior art.

The excitation efficiency has been analyzed, showing sensitivity to the mode matching conditions. In particular, we report a saturation power ($P_s$) of a factor of 12 smaller for molecules within the antenna of FIG. 19(d) with respect to the reference case of FIG. 19(a), i.e. $P_s$ decreases from 32±8 μW to 2.6±0.7 μW. On the other hand, there is no appreciable difference in the total collected power, given the high-NA of our microscope objective and the unmodified decay rate. In fact, the count rates at saturation are 3.1±0.5 Mcps (million counts per second) for the reference case of FIG. 3a and 2.8±0.7 Mcps for the directional antenna of FIG. 3d. All the data confirm the picture that the modified emission profile yields an increased coupling efficiency, e.g. with a weakly-focused laser beam or an optical fiber.

This is an evidence that the device according to the invention functions also as a receiver, i.e. the fluorescence molecule is now the receiver and a light beam is sent through the various elements down to the molecule (or other receiver).

Example 7

In general, in the device according to the invention, the distance between reflector and semi-opaque film (102) ranges from λ/(2.9n)+k*λ/(2n) to λ/(2.5n)+k*λ/(2n) and the distance between the one or more incoherent light emitters (105) and the reflector ranges from λ/(6n) to λ/(4n) if k<2 or from λ/(6n)+(k−2)*λ/(2n) to λ/(4n)+(k−2)*λ/(2n) if k≥2, wherein k is a natural number and n is the refractive index in the spacer medium. Each of the light emitters (or receivers, depending on the configuration of the invention device) may be within this ranges, but the distance may vary from emitter to emitter.

In FIG. 21 we plot the angular emission pattern, i.e. the electric field intensity on a reference sphere in the far field as a function of the dipole distances to the reflector ($d_1$) and director ($d_2$). Calculations are normalized to the maximum value of the emission in the case of a homogeneous medium with refractive index n=1.5. In particular, we perform a scan around the optimal geometry reported in FIG. 20 of the main text, i.e., reflector and director made of gold with thickness 100 nm and 20 nm respectively, spacer medium with n=1.5 and air above the director. If the total distance between the metallic element is kept constant, i.e. moving orthogonal to the diagonal of the 2D-plot matrix, there is only a weak dependence on the dipole position, confirming what presented in FIG. 4c of the manuscript. Focusing on a single raw or column of FIG. 21 instead, one can appreciate the sensitivity of the antenna response to the total distance D between reflector and director. In particular we calculate the emitted power integrated over the azimuthal coordinate and report it in FIG. 22 as a function of θ. Directional emission occurs already for a total thickness of 180 nm but with suppression of the total radiated power (solid curve). Both directivity and total collected power increase until the total thickness amounts to 200 nm (red solid curve). Even 10-nm higher values give rise to lobes in the emission patters, although the total collected power is kept constant (e.g., purple solid curve).

Interestingly, the beaming effect is recovered for a total thickness of 460 nm and approximately every λ/2n from the first optimal condition corresponding to D=200 nm (see FIG. 23). In particular we observe that directivity improves with increasing antenna length. The total emitted power however, represented by the area underlying the curves in FIG. 23, is not conserved. This could be due to either small effects on the local density of states or to the onset of guided modes in the spacer layer. For thicknesses higher than about 1.5 μm, the condition for constructive interference on the dipole position becomes more critical and the peaks at higher angles (already visible in FIG. 23) start to dominate.

The antenna director is a weakly reflective element, which configures the structure as a broadband device. In the proposed cost-effective design the director is made out of gold. The optimal gold thickness is the result of a compromise, which takes into account losses due to absorption in the metal, the desired broad wavelength response and the amplitude of the reflected field at the interface.

Advantages and Detailed Comparison with the Prior Art

To summarize, the main effects of the present invention are:

Modification of the radiation pattern of a sub wavelength emitter to channel its emission into a narrow cone;

This is obtained with a simple, robust, planar geometry that can be obtained with low-cost methods;

The performances do not depend on the lateral position of the emitter, which largely simplifies the implementation and application in devices;

The structure is broadband, meaning that a large collection efficiency is obtained in a broad spectral range;

There is a good tolerance in the structure parameters, meaning that the fabrication precision we need is fully compatible with standard procedures;

The result is general, meaning that it can be scaled to other wavelengths and materials.

Concerning the prior art, first we would like to explain the conceptual relevance of choosing the appropriate distance between the light source and the reflector.

Lower distance: when a light source is placed near a metal mirror, non-radiative energy transfer $P_{ET}$ from the source to the mirror sets in depending on distance d, emission wavelength and optical constants of the mirror $\varepsilon_m$ and the spacer medium $\varepsilon_b$, where the source is located. For the small separation under consideration, i.e. d<λ/(4n), the light field can be treated in the electrostatic approximation to find a simplified formula for the normalized transfer rate (R. R. Chance, et al., Adv. Chem. Phys. 37, 1 (1978)):

$$\frac{P_{ET}}{P} = \frac{s}{4(kd)^3} \operatorname{Im}\left\{\frac{\varepsilon_m - \varepsilon_b}{\varepsilon_m + \varepsilon_b}\right\} \quad (3)$$

wherein P is the power emitted by the light source in free space, k is the wave vector equal to 2πn/λ and s is equal to 3/2 or 3/4 for a light source with dipole perpendicular or parallel to the mirror, respectively. This process is known to rapidly decrease the fraction of power emitted to the far field and quenches the light source. This is exemplified in FIG. 18 for the cases of gold and aluminum reflectors discussed in FIGS. 11 and 12.

Furthermore, even for the case of an ideal mirror (i.e. without absorption), the power emitted by an oscillating dipole $P_{MIR}$ varies as a function of distance from that mirror according to the expression (for a dipole parallel to the interface) (R. R. Chance, et al., Adv. Chem. Phys. 37, 1 (1978)):

$$P_{MIR}/P = 1 - 3/2 Im[(-1/(2kd)^3 + i/(2kd)^2 + 1/(2kd))\text{Exp}[2ikd]], \quad (4)$$

wherein i is the imaginary unit. In practice, the image dipole induced in the mirror can be out of phase with respect to the oscillating dipole and when the distance vanishes the emitted power goes to zero, as shown in the plot of Eq. (4) in FIG. 18.

Therefore, the minimum distance $d_{min}$ that should be considered to be practical for beaming a light source by a mirror would correspond to the situation where $P_{ET}/P$ is smaller than 50% and $P_{MIR}/P$ is larger than 50%. Which one comes first depends on the absorption by real mirrors, which varies with wavelength and material. In other words, for distances smaller than $d_{min}$ the mirror would not give any advantage with respect to emission in free space. The Inventor have thus found that $\lambda/(6n)$ is a favorable distance to avoid quenching light emission and at the same time achieve beam forming.

Figure 18:
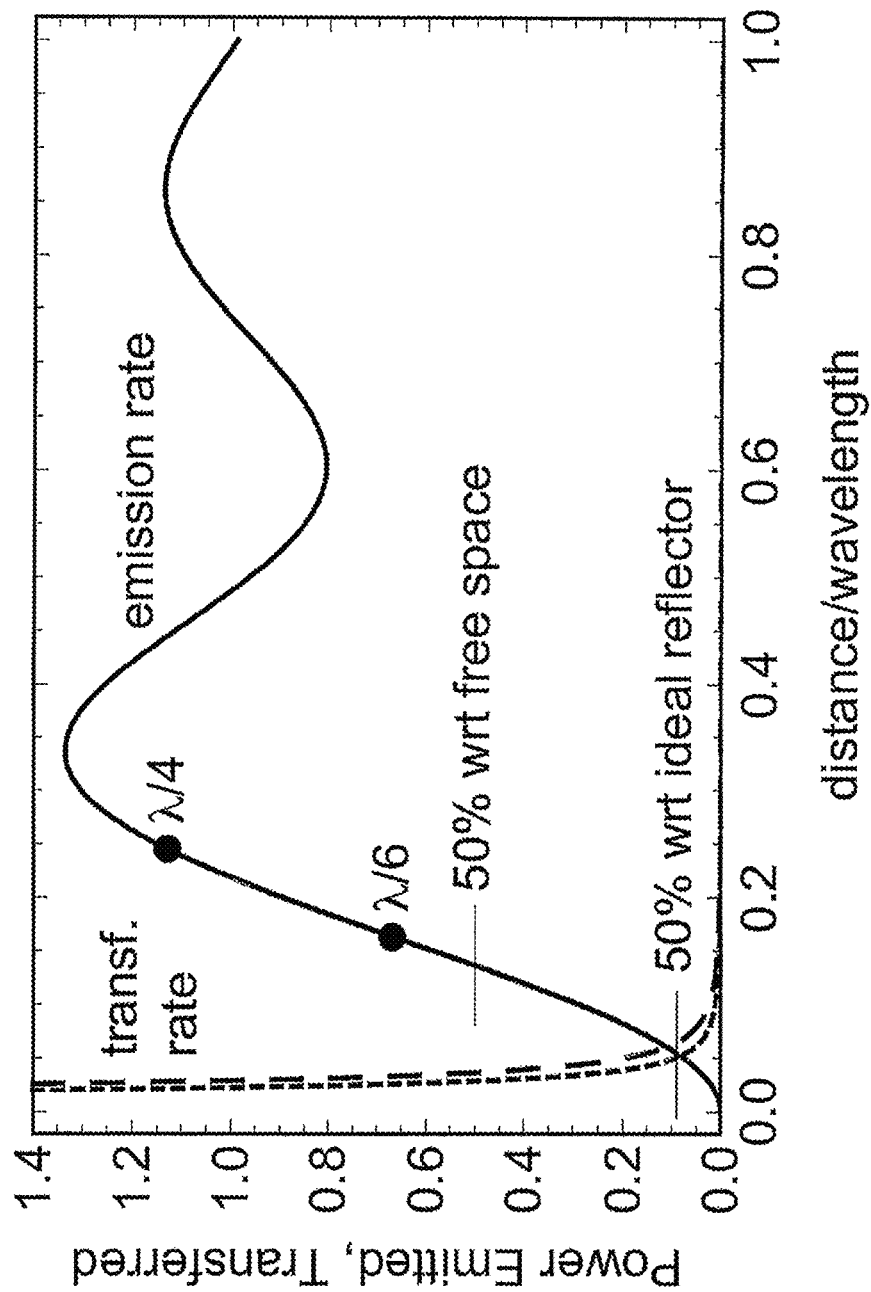
FIG. 18 shows the emission rate (solid curve) for an oscillating dipole parallel with respect to an ideal mirror as a function of distance from that mirror. The distance interval between $\lambda/(4n)$ and $\lambda/(6n)$ is indicated, as well as the point where the emission rate is 50% with respect to that in free space. Moreover, the dotted and dashed curves represent the power transfer rate to a real mirror made of gold and aluminum at $\lambda=785$ nm and $\lambda=530$ nm, respectively, according to equation (3). The distance where this rate is 50% of the emission rate with an ideal mirror is also indicated.

Upper distance: When the source is instead located at a distance of about $\lambda/(4n)$, the phase difference accumulated by the direct partial wave and the reflected partial wave corresponds to $\lambda/(2n)$ plus a phase shift of approximately $\pi$ (for an ideal mirror), which together give rise to constructive interference. Hence, the emission pattern is enhanced in the direction perpendicular to the mirror, giving rise to beam forming. We remark that a phase shift of $\pi$ refers to reflection on a perfect mirror. In the case of a real mirror, e.g. with reflectivity <100%, the phase shift at the mirror would depart from this ideal value, as inferred from the data of FIGS. 11 and 12, whereby the distance does not correspond exactly to $\lambda/(4n)$, but it has been experimentally verified that the maximum is around $\lambda/(3.5n)$. Furthermore, as shown in FIG. 18, even for an ideal mirror the maximum of the emission rate is not obtained exactly at $\lambda/(4n)$, because one has to take into account the near field of the light source when the distance from the mirror is smaller than $\lambda/(2n)$.

Large distances: When considering the light source as a superposition of plane waves, when that is placed at a distance $d_{max}$ larger than about $\lambda/(2n)$ from the mirror, the optical path difference between the light emitted directly to the far field and the light reflected by the mirror and then directed to the far field becomes larger than one wavelength, thus giving rise to destructive and constructive interference between the two partial waves. Moreover, for emission in the direction perpendicular to the metal mirror, the interference between the partial wave directly emitted to the far field and the partial wave reflected by the mirror and then directed in the same direction of the previous one is characterized by destructive interference, when the phase difference is given by an optical path difference of a multiple of $\lambda/n$ (constructive interference) plus a phase shift of approximately $\pi$ (destructive interference) due to reflection at the mirror. As a consequence, the emission pattern acquires a structure with lateral lobes and the central lobe is suppressed. On the contrary, the emission pattern may present a strong central lobe if the interference is constructive. However, starting from a certain distance the appearance of lateral lobes cannot be avoided, as exemplified in FIG. 23.

Next, we would like to point out why previous collection strategies that rely on other physical mechanisms did not consider this range of distances. The literature here cited (e.g. X.-W. Chen, et al., Opt. Lett. 36, 3545 (2011)), takes advantage of leaky waves created by a waveguide geometry positioned in front of a mirror. There, the authors were not seeking distances from the mirror of the order of $\lambda/(4n)$ to avoid perturbation of the guided modes in their leaky-waveguide design. In fact, it is commonly accepted that a distance of $\lambda/(2n)$ should be considered as the onset of near-field interaction of evanescent waves with nearby interfaces, e.g. respectively the guided wave and the mirror in that case.

On the other hand, distances shorter than $\lambda/(6n)$ have been pursued in order to detect fluorescence via near-field energy transfer to the mirror. In those cases, the mirror is actually a thin metal film that allows the energy to be transmitted to the other side of the mirror (see for example P. M Andres, et al., Science 302, 1002 (2004)). The range of the invention is to avoid this effect, as experienced by the Inventors.

Concerning the optimization of light extraction from organic light-emitting diodes (OLED), the work of S. McDaniel, et al., Opt. Express 18, 17477 (2010) points out the utility of placing a reflector at a distance of multiples of $\lambda/(4n)$, but the main results are focused on the function of a grating structure above the light source, without using a director element. Furthermore, they point out that $\lambda/(4n)$ refers to the maximum emission, which does not hold for our case where near-field interactions between the oscillating dipole and the mirror are fully taken into account.

The device according to the invention can be used to improve the excitation of light emitters, e.g., molecules, by an external source, such as a weakly focused Gaussian beam or an optical fibre (107—see FIG. 3) whose radiation is incident on the director.

BIBLIOGRAPHY

[1] W. L. Barnes, G. Björk, J. M. Gérard, P. Jonsson, J. A. E. Wasey, P. T. Worthing, V. Zwiller, Eur. Phys. J. D 18, 197 (2002)
[2] S. C. Kitson, W. L. Barnes, J. R. Sambles, Opt. Commun. 122, 147 (1996)
[3] H. Rigneault, F. Lemarchand, A. Sentenac, H. Giovannini, Opt. Lett. 24, 148 (1999)
[4] M. Rattier, Th. F. Krauss, J.-F. Carlin, R. Stanley, U. Oesterle, R. Houdré, Ch. J. M. Smith, R. M. De La Rue, H. Benisty, C. Weisbuch, Opt. Quantum Electron. 34, 79 (2002)
[5] M. Zelsmann, E. Picard, T. Charvolin, E. Hadji, M. Heitzmann, B. Dal Zotto, M. E. Nier, C. Seassal, P. Rojo-Romeo, X. Letartre, Appl. Phys. Lett. 83, 2542 (2003)
[6] A. M. Armani, R. P. Kulkarni, S. E. Fraser, R. C. Flagan, K. J. Vahala, Science 317, 783 (2007)
[7] C. A. Balanis, Antenna Theory—Analysis and Design (Wiley, 2005) pages 94-96.
[8] Xue-Wen Chen. S. Götzinger, V. Sandoghdar, Opt. Lett. 36, 3545 (2011)
[9] F. Bigourdan, F. Marquier, J.-P. Hugonin, J.-J. Greffet, Opt. Express 22, 2337 (2014)
[10] K. G. Lee, X. W. Chen, H. Eghlidi, P. Kukura, R. Lettow, A. Renn, V. Sandoghdar, S. Götzinger, Nat. Photon. 5, 166 (2011)
[11] M. Agio and A. Alù, Optical Antennas (Cambridge University Press (2013)
[12] Nat. Photon. 5, 166 (2011), Opt. Lett. 36, 3545 (2011)
[13] J. Li, A. Salandrino, N. Engheta, Phys. Rev. B 76, 245403 (2007)

[14] T. Kosako, Y. Kadoya, H. F. Hofmann, Nat. Photon. 4, 312 (2010)
[15] A. G. Curto, G. Volpe, T. H. Taminiau, M. P. Kreuzer, R. Quidant, N. van Hulst, Science 329, 930 (2010)
[16] S. McDaniel, S. Blair, Opt. Express 18, 17477 (2010)
[17] N. Guérin, S. Enoch, G. Tayeb, P. Sabouroux, P. Vincent, H. Legay, IEEE Trans. Antennas Propag. 54, 220 (2006)
[18] A. V. Kildishev, A. Boltasseva, V. M. Shalaev, Science 339, 1289 (2013)
[19] R. R. Chance, A. Prock, R. Silbey, Adv. Chem. Phys. 37, 1 (1978)
[20] P. M Andres, W. L. Barnes, Science 302, 1002 (2004)

In the foregoing, preferred embodiments have been described and variations to the invention have been suggested, however it is to be understood that those skilled in the art will be able to change the embodiments without falling outside the relevant scope of protection, as defined in the appended claims.

The invention claimed is:

1. A device for the beaming and collection of light emitted by light sources, comprising in the order along a direction of extension:
   at least a reflector,
   a spacer medium contiguous to the reflector;
   one or more incoherent or coherent light emitters emitting at wavelength $\lambda$ and placed in the spacer medium or contiguous to the spacer medium at a distance d from said at least a reflector;
   one or more optical receivers corresponding to the one or more incoherent or coherent light emitters;
   wherein:
   distance d is such that $\lambda/(6n) \leq d \leq \lambda/(4n)$, wherein n is the refraction index of the spacer medium;
   the reflectivity of the at least a reflector is larger than 80%;
   after the spacer medium along said extension direction, in front of the at least a reflector, a semi-opaque film is placed, which has a reflectivity in the range of 50-99% and a thickness smaller than $\lambda$,
   wherein the wavelength $\lambda$ is different from the resonance wavelength $\lambda_{RES}$ of the system comprising the reflector, the semi-opaque film and the spacer medium.

2. The device according to claim 1, wherein the one or more incoherent light emitters are passive, i.e. using an additional light source exciting it, or active.

3. The device according to claim 1, wherein the one or more optical receivers comprise at least a low-NA optical receiver, for example an optical fibre.

4. The device according to claim 1, wherein after the semi-opaque film along said extension direction, on the side not facing the at least a reflector, a planar film is placed, which has a thickness that is smaller than the wavelength $\lambda$ and such that the light crossing it undergoes a refraction such that it is focused.

5. The device according to claim 1, wherein the semi-opaque film has at least 50% of reflectivity, preferably 95%.

6. The device according to claim 1, wherein the reflectivity of the at least a reflector is larger than 90%.

7. The device according to claim 1, wherein said spacer medium is air and means are provided for making a fluidic sample flow in the air such that the one or more incoherent light emitters are delivered and removed by the same fluidic sample.

8. The device according to claim 1, wherein the spacer medium is layered.

9. The device according to claim 1, wherein the reflector is layered, for example comprising a layer of Au, a layer of Ag and an intermediate layer of a dielectric material.

10. The device according claim 1, wherein the semi-opaque film is layered, for example comprising a layer of Au, a layer of Ag and an intermediate layer of a dielectric material.

11. The device according claim 1, wherein the distance between reflector and semi-opaque film ranges from $\lambda/(2.9n)+k*\lambda/(2n)$ to $\lambda/(2.5n)+k*\lambda/(2n)$ and the distance between each of the one or more incoherent or coherent light emitters and the reflector ranges from $\lambda/(6n)$ to $\lambda/(4n)$ if $k<2$ or from $\lambda/(6n)+(k-2)*\lambda/(2n)$ to $\lambda/(4n)+(k-2)*\lambda/(2n)$ if $k \geq 2$, wherein k is a natural number and n is the refractive index in the spacer medium.

12. The device according to claim 11, wherein the distance between reflector and director ranges from $\lambda/(2.9n)$ and $\lambda/(2.5n)$ and from $\lambda/(1.3n)$ and $\lambda/(1.1n)$.

13. A device for the beaming and collection of light emitted by light sources, comprising in the order along a direction of extension:
   at least a reflector,
   a spacer medium contiguous to the reflector;
   one or more light receivers placed in the spacer medium or contiguous to the spacer medium at a distance d from said at least a reflector;
   one or more light sources emitting at wavelength $\lambda$ and corresponding to the one or more light receivers;
   distance d is such that $\lambda/(6n) \leq d \leq \lambda/(4n)$, wherein n is the refraction index of the spacer medium;
   the reflectivity of the at least a reflector is larger than 80%;
   after the spacer medium along said extension direction, in front of the at least a reflector, a semi-opaque film is placed, which has a reflectivity in the range of 50-99% and a thickness smaller than $\lambda$,
   wherein the wavelength $\lambda$ is different from the resonance wavelength $\lambda_{RES}$ of the system comprising the reflector, the semi-opaque film and the spacer medium.

14. The device according to claim 13, wherein after the semi-opaque film along said extension direction, on the side not facing the at least a reflector, a planar film is placed, which has a thickness that is smaller than the wavelength $\lambda$ and such that the light crossing it undergoes a refraction such that it is focused.

15. The device according to claim 13, wherein the semi-opaque film has at least 50% of reflectivity, preferably 95%.

16. The device according to claim 13, wherein the semi-opaque film is layered, for example comprising a layer of Au, a layer of Ag and an intermediate layer of a dielectric material.

17. The device according to claim 13, wherein the distance between reflector and semi-opaque film ranges from $\lambda/(2.9n)+k*\lambda/(2n)$ to $\lambda/(2.5n)+k*\lambda/(2n)$ and the distance between each of the one or more light receivers and the reflector ranges from $\lambda/(6n)$ to $\lambda/(4n)$ if $k<2$ or from $\lambda/(6n)+(k-2)*\lambda/(2n)$ to $\lambda/(4n)+(k-2)*\lambda/(2n)$ if $k \geq 2$, wherein k is a natural number and n is the refractive index in the spacer medium.

18. The device according to claim 17, wherein the distance between reflector and director ranges from $\lambda/(2.9n)$ and $\lambda/(2.5n)$ and from $\lambda/(1.3n)$ and $\lambda/(1.1n)$.

* * * * *